US009179915B2

(12) United States Patent
Edoga et al.

(10) Patent No.: US 9,179,915 B2
(45) Date of Patent: Nov. 10, 2015

(54) ENDOVASCULAR STAPLER

(75) Inventors: John K. Edoga, Morristown, NJ (US);
Thierry Richard, Florham Park, NJ
(US); Alan Bachman, Milford, CT (US)

(73) Assignee: EDRICH HEALTH TECHNOLOGIES, INC., Morristown, NJ (US)

( * ) Notice: Subject to any disclaimer, the term of this patent is extended or adjusted under 35 U.S.C. 154(b) by 246 days.

(21) Appl. No.: 13/562,085

(22) Filed: Jul. 30, 2012

(65) Prior Publication Data
US 2013/0060324 A1 Mar. 7, 2013

Related U.S. Application Data

(60) Continuation of application No. 11/446,482, filed on Jun. 2, 2006, now abandoned, which is a division of application No. 10/837,827, filed on May 3, 2004, now Pat. No. 8,627,992, which is a continuation-in-part of application No. 10/737,466, filed on Dec. 16, 2003, now Pat. No. 7,399,310.

(60) Provisional application No. 60/433,692, filed on Dec. 16, 2002, provisional application No. 60/501,060, filed on Sep. 8, 2003.

(51) Int. Cl.
*A61B 17/115* (2006.01)
*A61F 2/95* (2013.01)
(Continued)

(52) U.S. Cl.
CPC .............. *A61B 17/10* (2013.01); *A61B 17/068* (2013.01); *A61B 17/0644* (2013.01); *A61B 17/0684* (2013.01); *A61B 17/115* (2013.01); *A61B 19/54* (2013.01); *A61B 2017/00557* (2013.01); *A61B 2017/00867* (2013.01); *A61B 2017/0649* (2013.01); *A61B 2017/1157* (2013.01); *A61B 2017/22051* (2013.01); *A61B 2017/22052* (2013.01); *A61B 2017/22069* (2013.01); *A61B 2017/2905* (2013.01);
(Continued)

(58) Field of Classification Search
CPC .. A61B 17/068; A61B 17/0682; A61B 17/08; A61B 17/083; A61B 17/10; A61B 17/105; A61B 17/11; A61B 17/0644; A61F 2/07; A61F 2/95
USPC ......... 606/139, 142, 143, 151, 157, 158, 213, 606/219; 227/175.1–175.4, 176.1
See application file for complete search history.

(56) References Cited

U.S. PATENT DOCUMENTS 5,360,443 A * 11/1994 Barone et al. ................ 623/1.13
5,577,654 A * 11/1996 Bishop ....................... 227/175.1
(Continued)

FOREIGN PATENT DOCUMENTS

WO    WO 0007506 A2 * 2/2000

*Primary Examiner* — Kathleen Holwerda
(74) *Attorney, Agent, or Firm* — McCarter & English, LLP

(57) ABSTRACT

An endovascular stapler for securing an endograft to a vessel is disclosed. The stapler includes a staple housing adapted for storing at least one staple therein, the staple housing having an exit area for discharge of the at least one staple therethrough, an actuating assembly adapted for discharging the at least one staple through the exit area, and a displacement mechanism in operative association with the staple housing near the exit area. The displacement member is operative for pushing the exit area against the endograft when discharging the at least one staple therethrough. The discharged staple forms a plurality of opposed loops connected by a central element upon discharge. Also disclosed are staples and displacement mechanisms adapted for use with surgical instruments such as the present endovascular staplers. The staples may be formed from memory metal or other metal. The displacement mechanisms disclosed include balloons and rigid offsetting devices.

19 Claims, 35 Drawing Sheets

(51) Int. Cl.
*A61B 17/10* (2006.01)
*A61B 17/064* (2006.01)
*A61B 17/068* (2006.01)
*A61B 19/00* (2006.01)
*A61B 17/00* (2006.01)
*A61B 17/22* (2006.01)
*A61B 17/29* (2006.01)
*A61F 2/07* (2013.01)

(52) U.S. Cl.
CPC  *A61B 2017/2933* (2013.01); *A61B 2019/5425* (2013.01); *A61F 2/07* (2013.01)

(56) References Cited

U.S. PATENT DOCUMENTS

| | | | | |
|---|---|---|---|---|
| 5,997,556 | A * | 12/1999 | Tanner | 606/153 |
| 6,059,504 | A * | 5/2000 | Ishida et al. | B42B 5/08 227/119 |
| 6,149,660 | A * | 11/2000 | Laufer et al. | 606/143 |
| 6,626,916 | B1 * | 9/2003 | Yeung et al. | 606/139 |
| 6,638,297 | B1 * | 10/2003 | Huitema | 606/219 |
| 6,960,217 | B2 * | 11/2005 | Bolduc | 606/108 |
| 7,736,377 | B1 * | 6/2010 | Anson et al. | 606/219 |
| 2002/0029048 | A1 * | 3/2002 | Miller | 606/138 |

* cited by examiner

SECTION A/A'

SECTION B/B'

SECTION C/C'

SECTION D/D'

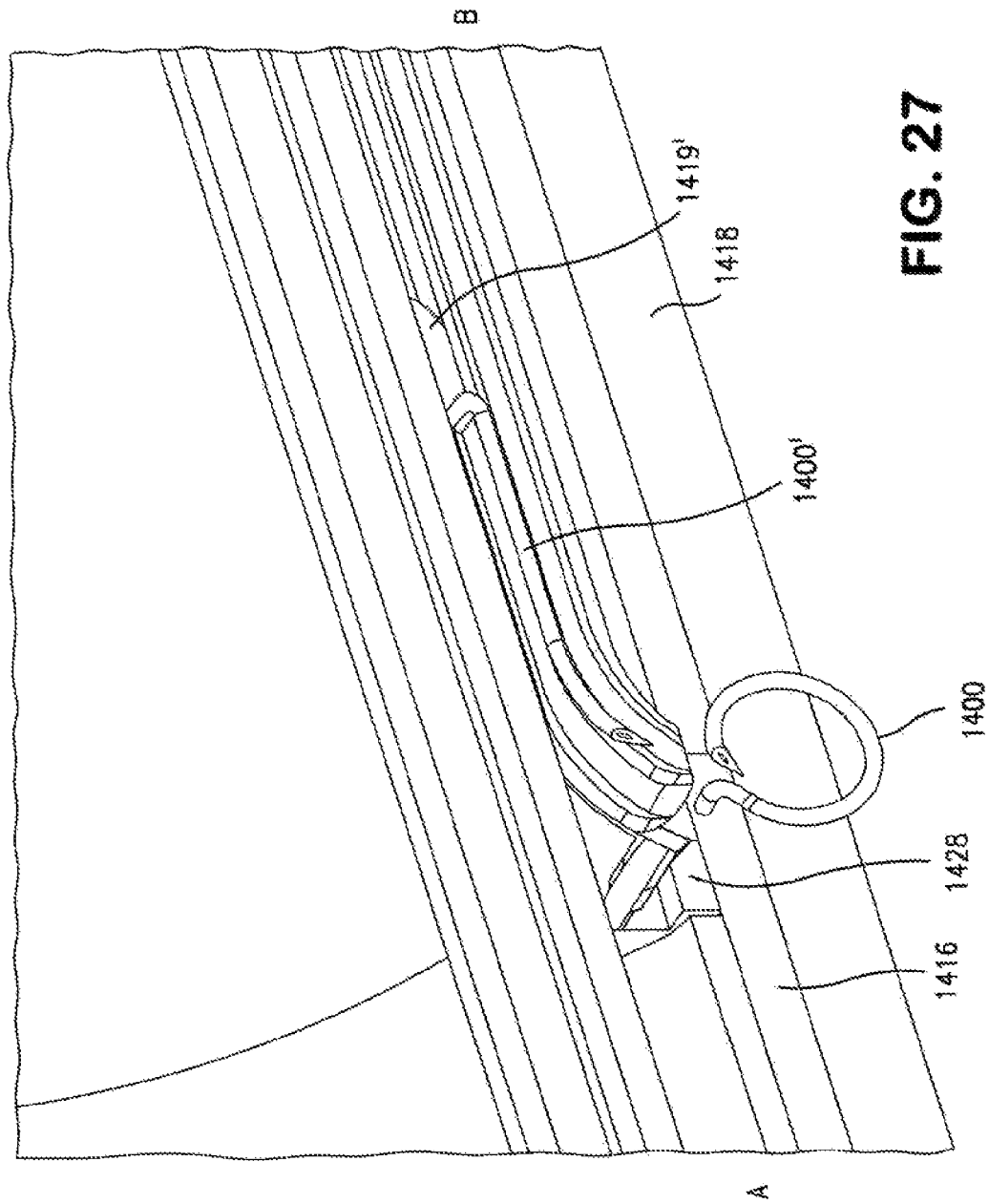

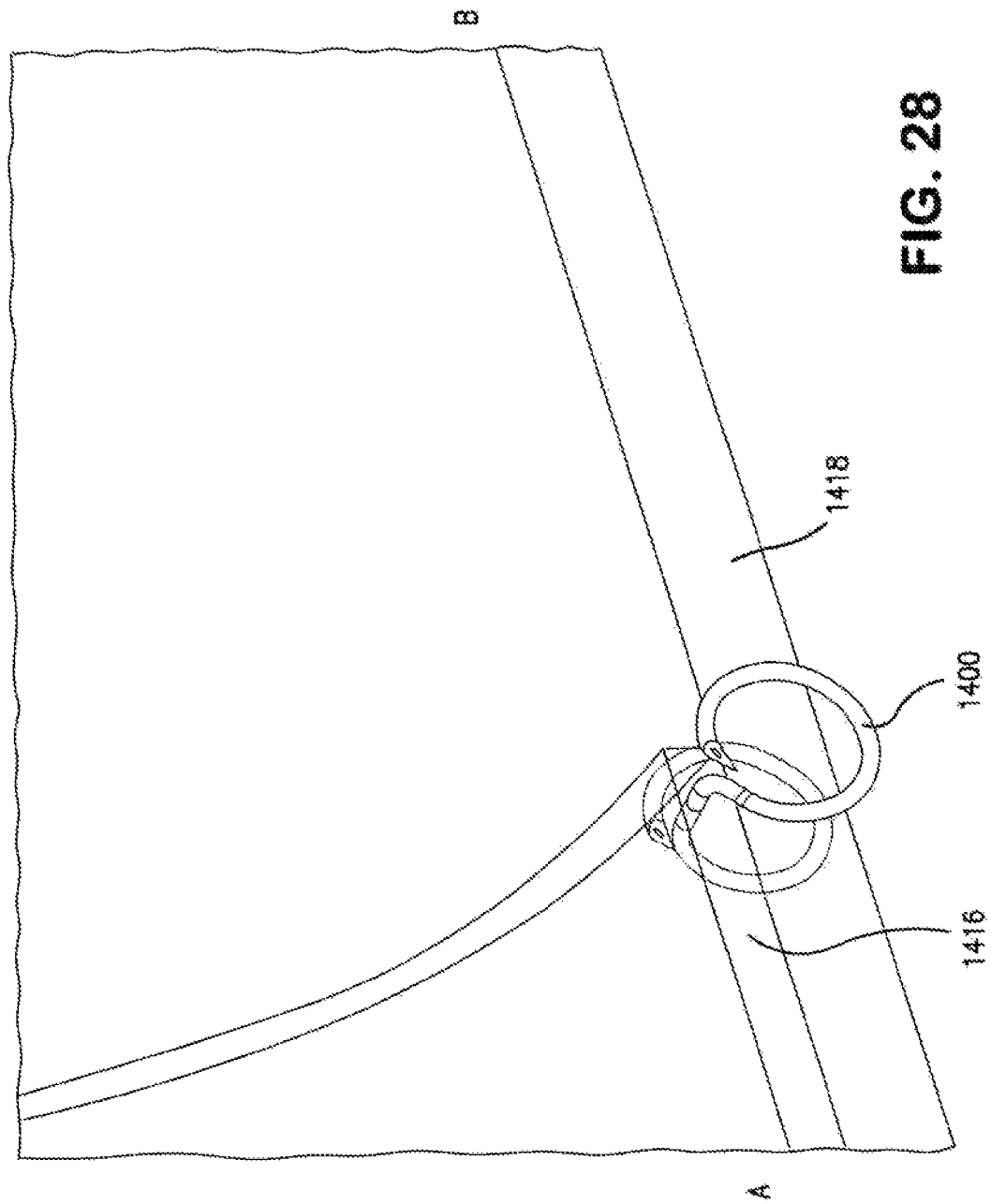

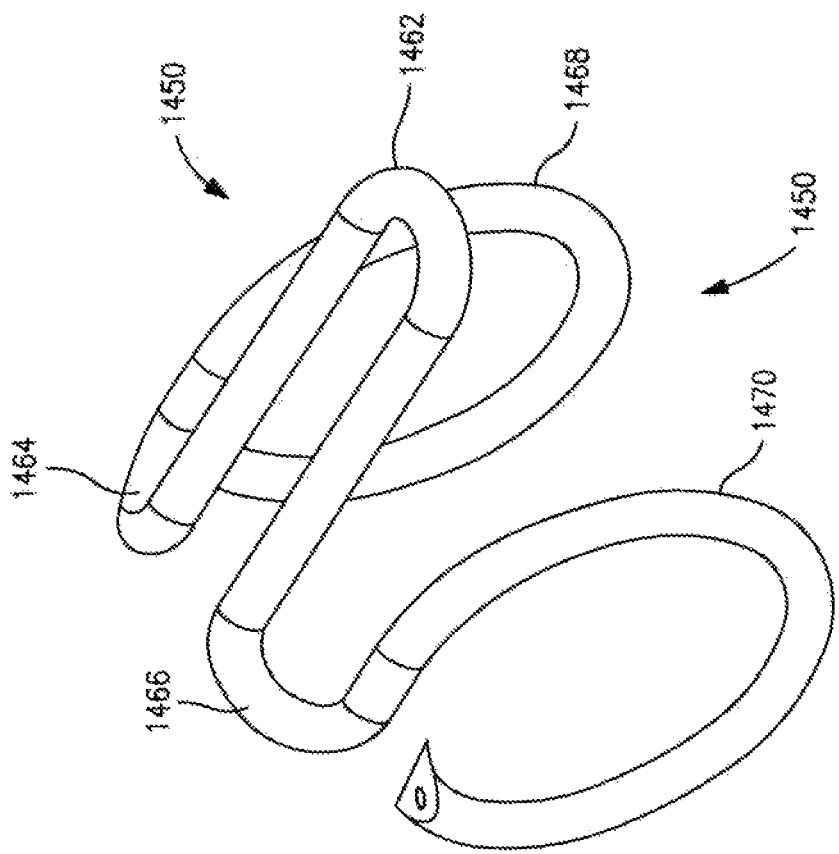
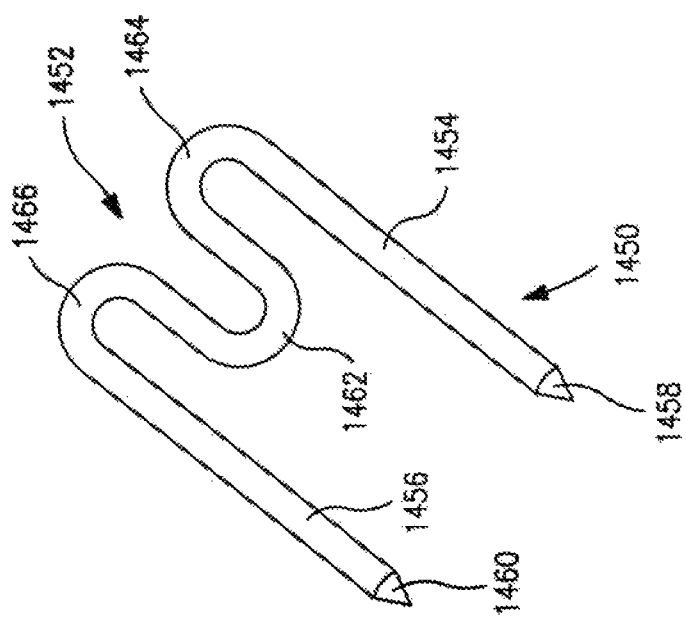

ENDOVASCULAR STAPLER

CROSS REFERENCE TO RELATED APPLICATIONS

The present patent application is continuation of and claims the benefit of priority to U.S. patent application Ser. No. 11/446,482, filed Jun. 2, 2006, which in turn is a divisional application of and claims the benefit of priority to U.S. patent application Ser. No. 10/837,827, filed May 3, 2004, which in turn is a continuation-in-part of and claims the benefit of priority to U.S. patent application Ser. No. 10/737,466 filed Dec. 16, 2003, which in turn claims the benefit of priority to U.S. Provisional Patent Application Ser. No. 60/433,692 filed Dec. 16, 2002, and U.S. Provisional Application No. 60/501,060 filed Sep. 8, 2003. The disclosure of each of the foregoing patent applications is hereby incorporated herein by reference in its entirety for any purpose whatsoever.

The present invention relates to a stapling device for use in the fixation of endovascular grafts to the walls of vessels. Fixation of grafts utilizing the present invention may be conducted during initial implantation. In addition, the present invention may also be utilized to arrest the vexing complication of proximal or distal migrations following the prior implantation of such grafts. Fixation may also be conducted to repair Type 1 endoleaks not caused by migration.

It is well known that endovascular grafts may be inserted into the human body during numerous medical procedures. Grafts are typically inserted into vessels and held in place by friction, such as with self-expanding or balloon expandable stents. The grafts may also be affixed to vessels with hooks or barbs.

The grafts may be formed from synthetic materials, such as polyester, expanded polytetrafluoroethylene ("ePTFE"), or others. The grafts may also be formed of natural vessels harvested from other areas of the body or from a donor mammal. Notwithstanding the various materials utilized, migration of the grafts over time remains a problem.

Caudad device migration is known to lead to a Type 1 endoleak with aneurysm sac reperfusion, enlargement and rupture. Cephalad device migration may lead to coverage of the renal artery orifices and renal insufficiency.

Such device migration is caused by many factors. One known factor is poor patient selection. Patients with cone shaped aortic necks, severe neck tortuosity, short necks or who have a laminated thrombus present at the landing site are generally susceptible to device migration problems. Other device migration issues are caused by changing aortic morphology following device implantation. Finally, migration may be caused by device structural fatigue and device design related issues. Even absent these conditions, device migration has been found.

Treatment of caudad migrations have traditionally been conducted by the addition of "sleeves" to the proximal end of the graft in an effort to regain purchase between the graft and the vessel it is attached to in order to maintain a seal between the two. More drastic options include resorting to conventional surgery. These late conversions are, unfortunately, associated with a high mortality rate.

Treatment options for the cephalad migrations are even less attractive. In the face of continued migration, resignation may be the only option as such migration may lead to renal insufficiency requiring hemodialysis. To permit device removal, a typical conversion in this case involves supraceliac aortic cross-clamping, and its associated problems.

Prior attempts at fixation of migrating devices, including additions of hooks, barbs, tackers, and other fastening devices have proven to be insufficient or impractical. It would therefore be advantageous to provide an endovascular stapling device which may be used to adequately arrest existing migrations, as well as secure new grafts in a manner likely to eliminate future migration. Actual fixation of the graft to the aortic neck at multiple points will also prevent the aorta itself from enlarging.

SUMMARY OF THE INVENTION

The endovascular stapler of the present invention is designed to overcome the deficiencies of the prior art. In one embodiment, an endovascular stapler for securing an endograft to a vessel comprises a staple housing adapted for storing at least one staple therein, the staple housing having an exit area for discharge of the at least one staple therethrough, an actuating assembly adapted for discharging the at least one staple through the exit area, and a displacement mechanism in operative association with the staple housing near the exit area, the displacement member operative for pushing the exit area against the endograft when discharging the at least one staple therethrough, wherein the discharged staple forms a plurality of opposed loops connected by a central element.

The displacement mechanism may comprise a balloon positioned near the exit area, the balloon adapted to be selectively inflated and deflated. The balloon may be offset from the staple housing by spokes, the spokes adapted to permit blood flow therebetween.

The staple may be deformed into two parallel straight legs connected by a central element while stored in the stapler housing.

The actuating assembly may comprise a pusher and a trigger, the pusher adapted to be advanced by the trigger to discharge the at least one staple.

The central element may be adapted to compress the endograft against the vessel after being discharged from the endovascular stapler.

In another embodiment, an endovascular stapler for securing an endograft to a vessel comprises a trigger housing comprising a trigger mechanism within the housing, a staple housing having a proximal end and a distal end, the staple housing coupled at the proximal end of the staple housing to the trigger housing, the staple housing adapted to store a staple, the staple housing having a staple exit area formed therein near the distal end thereof, a balloon exterior to the staple housing near the distal end thereof, the balloon adapted to be selectively inflated and deflated to push the staple exit area against the endograft, wherein the trigger mechanism may be actuated to drive a staple from the staple housing through the staple exit area into the endograft and the vessel, the staple returning approximately to its natural condition of having a plurality of opposed loops connected by a central element upon discharge.

The balloon may be noncompliant.

The staple may be deformed into two parallel straight legs connected by a central element while stored in the stapler housing. The discharged staple may comprise a pair of leading points adapted to penetrate the endograft and the vessel.

The balloon may be positioned opposite to the staple exit area.

The endovascular stapler may further comprise an output boss penetrating the trigger housing, a guide wire exit port near the distal end of the staple housing, a guide wire channel extending from the guide wire exit port to the output boss, and a guide wire extending within the guide wire channel, wherein the staple housing may be guided to a particular location within the vessel by sliding the staple housing along the guide wire.

The staple housing may be flexible.

The trigger assembly may further comprise a pusher operatively engaged with a trigger, the pusher extending from within the trigger housing to the staple exit area, wherein the pusher is adapted to advance through the staple housing to push the staple from the staple exit area.

The pusher may further comprise a first portion adjacent to the staple and a second portion behind the first portion, the second portion including a series of toothed elements.

The toothed elements may include angled portions angled away from the first portion.

The trigger assembly may further comprise a trigger having a grip exterior to the housing and an inner section interior to the housing, an outer section slideable about a portion of the inner section of the trigger, the outer section having a surface with toothed elements adapted to engage the toothed elements of the second section of the pusher, a spring situated between the outer section and the inner section of the trigger, and a pin about which the trigger, the outer section, and the spring may rotate, wherein the trigger housing may further comprise a handle and the toothed elements of the outer section advance the pusher to an advanced position toward the distal end of the staple housing when the trigger is rotated toward the handle.

The spring may permit the outer section to ratchet about the inner section of the trigger when the trigger is moved away from the handle, such that the pusher remains in the advanced position.

In a still further embodiment, an endovascular stapler for securing an endograft to a vessel may comprise a trigger housing comprising a trigger mechanism, a staple housing having a proximal end at the trigger housing and a distal end remote from the trigger housing, the staple housing comprising a staple channel adapted to store a plurality of staples in tandem, the staples each having a pair of parallel legs connected by a central portion, the staple channel extending from the proximal end of the staple housing to a staple exit area near the distal end of the staple housing, and a pusher extending into the staple channel from within the trigger housing, wherein the pusher is adapted to advance through the staple channel upon actuation of the trigger mechanism to advance the plurality of staples stored in tandem in the staple channel such that a first staple may be discharged through the staple exit area.

The staple channel may further comprise a curved portion adjacent the staple exit area, the curved portion configured to permit the staples to return to their natural condition as they are discharged from the staple exit area.

The discharged staples may penetrate the endograft and the vessel.

The discharged staples may include rings capable of penetrating the endograft and the vessel.

The endovascular stapler may further comprise a balloon inflation port penetrating the trigger housing, a balloon inflation channel extending within the staple housing and in fluid communication with the balloon inflation port, and a balloon exterior to the staple housing and in fluid communication with the balloon inflation channel, wherein the balloon may be selectively inflated and deflated to push the staple exit area against the endograft.

The balloon may be positioned opposite to the staple exit area.

The endovascular stapler may further comprise an output boss penetrating the trigger housing, a guide wire exit port near the distal end of the staple housing, a guide wire channel extending within the staple housing from the output boss to the guide wire exit port, and a guide wire extending within the guide wire channel, wherein the staple housing may be guided to a vessel by sliding the staple housing along the guide wire.

The guide wire channel may be substantially parallel to the staple channel.

The guide wire channel may extend beyond the staple exit area.

The guide wire channel may be adjacent to the staple exit area.

The endovascular stapler may further comprise a balloon inflation port penetrating the trigger housing, a balloon inflation channel extending within the staple housing and in fluid communication with the balloon inflation port, a balloon exterior to the staple housing and in fluid communication with the balloon inflation channel, an output boss penetrating the housing, a guide wire exit port near the distal end of the staple housing, a guide wire channel extending within the staple housing from the output boss to the guide wire exit port, and a guide wire extending within the guide wire channel, wherein the balloon may be selectively inflated and deflated to push the staple exit area against the endograft and the staple housing may be guided to a vessel by sliding the staple housing along the guide wire.

The pusher may further comprise a first portion and a second portion, the first portion being situated between the second portion and the staples, the second portion being predominantly flat in profile with a plurality of toothed elements.

The toothed elements may comprise ramped portions angled away from the first portion.

The trigger assembly may further comprise a trigger having a grip exterior to the trigger housing and an inner section interior to the housing, an outer section covering and slideable about the inner section of the trigger, the outer section having a surface with toothed elements having configurations such that the toothed elements of the outer section abut the toothed elements of the pusher, a spring situated between the outer section and the inner section of the trigger, and a pin about which the trigger, the outer section, and the spring may rotate, wherein the housing further comprises a handle and the toothed elements of the outer section advance the pusher toward the distal end of the staple housing when the trigger is moved toward the handle.

The spring may permit the outer section to ratchet about the inner section of the trigger when the trigger is moved away from the handle, such that the pusher remains in a fixed position.

The trigger mechanism may further comprise a spring associated with the trigger, the spring biasing the trigger away from the handle.

The second portion of the pusher may be stored in a staging area within the trigger housing.

The second portion of the pusher may be adapted to spiral within the staging area.

In another embodiment, an endovascular stapler for connecting a stent graft to a vessel may comprise a trigger housing having an elongate staple housing extending therefrom, the elongate staple housing having a staple exit area adapted to be inserted into a vessel, the elongate staple housing adapted to store a staple having parallel legs connected by a central portion, a pusher extending within the staple housing from the trigger housing, a trigger mechanism within the housing, the trigger mechanism adapted to advance the pusher within the staple housing to push a staple stored in the elongate staple housing through the staple exit area to connect the stent graft to the vessel, and a balloon adjacent the staple housing, the balloon inflatable to force the staple exit area against the stent graft.

The staple exit area may be adapted to permit the staple to return to its natural condition upon exiting the staple exit area.

The natural condition may comprise a pair of opposed loops connected by a central portion.

A still further embodiment of the present invention discloses a method of repairing an endograft in a vessel with an endovascular stapler having a distal end and a biasing mechanism associated therewith, the method comprising inserting the distal end of the endovascular stapler into the endograft, advancing the biasing mechanism so as to push the distal end of the endovascular stapler against the endograft without completely inhibiting blood flow, discharging a staple from the endovascular stapler into the endograft such that the staple forms a pair of curved legs connected by a central portion.

The method may also include the steps of partially retracting the biasing mechanism to permit rotation of the distal end of the endovascular stapler, rotating the distal end of the endovascular staple, advancing the biasing mechanism so as to push the distal end of the endovascular stapler against the endograft without completely inhibiting blood flow, discharging a staple from the endovascular stapler into the endograft such that the staple forms a pair of curved legs connected by a central portion.

A further embodiment discloses a method of repairing an endograft in a vessel with an endovascular stapler having a distal end forming a staple exit area, a trigger for deploying staples, and a balloon near the staple exit area, the method comprising inserting the distal end of the endovascular stapler into the endograft, inflating the balloon to push the staple exit area against the endograft, and deploying a staple from the staple exit area into the endograft and the vessel such that the staple forms a pair of curved legs connected by a central portion.

The method of repairing a vessel may further comprise partially deflating the balloon, rotating the endovascular stapler, reinflating the balloon so as to push the stapler exit area against the endograft in a location adjacent to the first staple, and deploying a second staple from the staple exit area into the endograft and the vessel, the second staple forming a pair of curved legs connected by a central portion upon deployment.

In yet another method of the present invention, surgery may be performed on a vessel having an endograft therein, the method comprising providing a plurality of staplers, each stapler having a stapler housing storing a U-shaped staple having a pair of legs connected by a central portion and a balloon capable of being inflated and deflated, inserting the stapler housing of the first of the plurality of staplers into the endograft, inflating the balloon of the first of the plurality of staplers so as to push the stapler housing against the endograft, advancing the first staple from within the stapler housing such that the legs of the first staple form loops piercing the endograft and the vessel wall.

The method may further comprise deflating the balloon, removing the stapler housing of the first of the plurality of staplers from the endograft, inserting the second of the plurality of stapler housings into the endograft, inflating the balloon so as to push the second of the plurality of stapler housings against the endograft in an area other than at the location of the first staple, advancing the staple of the second of the plurality of staplers from within the stapler housing such that the legs of the second staple form loops piercing the endograft.

In another embodiment of the present invention, an endovascular stapler for securing an endograft to a vessel may comprise a staple housing adapted for storing a plurality of staples having a pair of legs connected by a central portion therein, the staple housing having a plurality of exit areas for discharge of the plurality of staples therethrough, an actuating assembly adapted for discharging the plurality of staples through the plurality of exit areas, the actuating assembly comprising a plurality of staple pushers adapted to advance the plurality of staples through the plurality of exit areas and a trigger adapted to advance the plurality of staple pushers, and a displacement mechanism in operative association with the staple housing near the exit areas, the displacement mechanism operative for pushing the exit areas against the endograft when discharging the plurality of staples therethrough, wherein the plurality of staples each form a pair of loops connected by a central portion upon discharge.

The plurality of staples may be arranged radially about a longitudinal centerline of the staple housing.

The plurality of staples may be arranged linearly within the staple housing.

The displacement mechanism may comprise a first rod and a second rod pivotally connected by a pin, the first rod and the second rod having a first relation where the rods are substantially parallel and a second relation where the rods are angled with respect to each other, the rods pushing the exit areas against the endograft when in the angled relation.

In another embodiment of the present invention, a staple for connecting an endograft to a vessel may comprise a first condition in which the staple is U-shaped with a pair of straight legs connected by a central portion and a second condition in which the straight legs are formed into loops.

The central portion may form a tongue adapted to apply pressure upon material contained between the loops and the tongue.

Each of the loops may include an upper portion nearest the central portion, and the central portion may be at approximately the same elevation as the upper portions of each of the loops.

The staple may be made from a memory alloy.

The staple may be made from Nitinol.

The second condition may be the staple's natural condition.

In still another embodiment of the present invention, a balloon for use with a surgical device may comprise an inflatable section adapted to be inflated and an offsetting section, the offsetting section adapted to offset the balloon from the surgical device while permitting fluid flow between the inflatable section and the surgical device.

The offsetting section may comprise at least one spoke.

One of the at least one spoke may be metal or rigid biocompatible plastic.

One of the at least one spoke may be in fluid communication with the balloon such that the balloon may be selectively inflated and deflated through the spoke.

In another embodiment of the present invention, a biasing mechanism for use with a surgical instrument adapted for use within the lumen of a vessel may comprise a balloon adapted to be selectively inflated and deflated, at least one spoke tethering the balloon to the surgical instrument, the biasing mechanism having a first condition in which the balloon is deflated such that the surgical instrument is free to rotate within the lumen of the vessel, and the biasing mechanism having a second condition in which the balloon is inflated and offset from the surgical instrument such that fluid may flow between the balloon and the surgical instrument, the surgical instrument being inhibited from rotating within the lumen of the vessel in the second condition.

One of the at least one spokes may be in fluid communication with the balloon.

One of the at least one spokes may be metal.

In another embodiment of the present invention, a biasing mechanism for use with a surgical instrument adapted for use within the lumen of a vessel may comprise a first rod and a second rod pivotally connected by a pin, the first rod and the second rod having a first relation where the rods are substantially parallel and a second relation where the rods are angled with respect to each other, the rods pushing the surgical instrument against the endograft when in the second relation.

Blood may be permitted to flow around the biasing mechanism in the first relation and the second relation.

The biasing member may further comprise a third relation between the first relation and the second relation, the third relation permitting rotation of the surgical instrument within the lumen of the vessel.

In accordance with still further embodiments of the present invention, a method of attaching an endograft to a vessel wall with an endovascular stapler having a distal end and a proximal end with a biasing mechanism associated therewith, the method comprising inserting the distal end of the endovascular stapler into the endograft, activating the biasing mechanism so as to push the distal end of the endovascular stapler against the endograft, and discharging a first staple having a pair of legs connected by a central portion from the endovascular stapler into the endograft and vessel such that the staple legs form a pair of circular loops connected by the central portion.

The method may further comprise the steps of partially deactivating the biasing mechanism to permit rotation of the distal end of the endovascular stapler, rotating the distal end of the endovascular stapler, reactivating the biasing mechanism so as to push the distal end of the endovascular stapler against the endograft, and discharging a second staple having a pair of legs connected by a central portion from the endovascular stapler into the endograft and vessel such that the staple legs form a pair of circular loops connected by the central portion.

The first staple may be constructed from a memory alloy. The legs of the first staple may be predominantly straight while within the stapler prior to the step of discharging. The natural condition of the first staple may be where the legs form circular loops. The step of discharging may permit the first staple to return to its natural condition.

The step of discharging may serve to advance a staple pusher within the stapler for discharging the first staple. The first staple may advance along a staple guide, the staple guide retarding the return of the first staple to its natural condition. The staple pusher may include a pivoting portion and the step of discharging may rotate the pivoting portion into the central portion of the first staple such that the central portion of the first staple abuts the endograft.

The straight legs may be substantially parallel to the longitudinal axis of the endograft during the step of inserting.

The endovascular stapler may include a removable cartridge containing a plurality of staples, each of the staples having a pair of legs connected by a central portion. The legs of the plurality of staples may be predominantly straight while within the stapler cartridge. The natural condition of the plurality of staples may be where the legs form circular loops, and the step of discharging may permit the first staple to return to its natural condition.

The cartridge may be replaceable.

The vessel may flow blood from a heart and the step of discharging may drive the first staple toward the heart against the direction of blood flow.

The step of discharging may be conducted by a trigger mechanism that pushes a staple pusher.

The vessel may flow blood from a heart and the step of discharging may drives the first staple away from the heart in the direction of blood flow.

The step of discharging may be conducted by a trigger mechanism that pulls a staple pusher.

The legs of the discharged first staple may form a plane extending parallel to the longitudinal axis of the endograft following the step of discharging.

The step of discharging may advance the staple through a staple exit area, the staple exit area being radio opaque.

The vessel may flow blood and the step of activating the biasing mechanism may not completely inhibit blood flow.

The vessel may flow blood and the steps of activating the biasing mechanism and reactivating the biasing mechanism may not completely inhibit blood flow.

The pair of circular loops may be closed.

The circular loops may be partial circular loops.

In accordance with a still further aspect of the present invention, a method of attaching an endograft to a vessel wall with an endovascular stapler having a distal end forming a staple exit area along a side thereof, a proximal end with a trigger for deploying staples, and a balloon near the staple exit area, may comprise inserting the distal end of the endovascular stapler into the endograft, inflating the balloon to push the staple exit area against the endograft, and deploying a first staple from the staple exit area into the endograft and the vessel wall such that the first staple forms a pair circular loops connected by a central portion.

The circular loops may be partial circular loops.

The circular loops may be closed.

The method may further comprise partially deflating the balloon, rotating the endovascular stapler, reinflating the balloon so as to push the staple exit area against the endograft in a location different from but adjacent to the deployed first staple, and deploying a second staple from the staple exit area through the endograft and the vessel wall, the second staple forming a pair of loops connected by a central portion upon deployment.

The first staple may be constructed from a memory alloy.

The natural condition of the first staple may be where the legs form circular loops.

The step of deploying may be conducted by activating the trigger to manipulate a staple pusher, the staple pusher pushing the first staple.

The staple pusher may include a pivoting portion and the step of deploying may rotate the pivoting portion into the staple such that the central portion of the staple abuts the endograft.

The vessel may flow blood from a heart and the step of deploying may drive the first staple toward the heart against the direction of blood flow.

The vessel may flow blood from a heart and the step of deploying may drive the first staple away from the heart in the direction of blood flow.

The circular legs of the first staple may form planes extending parallel to the longitudinal axis of the endograft following the step of discharging.

The staple exit area may be radio opaque.

The endovascular stapler may include a removable cartridge containing a plurality of staples, each of the staples having a pair of legs connected by a central portion.

The removable cartridge may be replaceable.

The step of deploying may serve to advance a staple pusher within the stapler for deploying the first staple.

The first staple may be formed from a memory alloy and the natural condition of the first staple may be where the legs form circular loops, the first staple legs being predominantly straight while within the stapler, the first staple advancing along a staple guide during the step of deploying, the staple guide retarding the return of the first staple to its natural condition.

In accordance with additional aspects of the present invention, a method of performing surgery on a vessel having an endograft therein, may comprise providing a plurality of staplers, each stapler having a stapler housing storing a U-shaped staple having a pair of legs connected by a central portion and a balloon capable of being inflated and deflated, inserting the stapler housing of the first of the plurality of staplers into the endograft, inflating the balloon of the first of the plurality of staplers so as to push the stapler housing against the endograft, and advancing the first staple from within the stapler housing such that the legs of the first staple form loops piercing the endograft and the vessel.

The method may further comprise deflating the balloon, removing the stapler housing of the first of the plurality of staplers from the endograft, inserting the second of the plurality of stapler housings into the endograft, inflating the balloon so as to push the second of the plurality of stapler housings against the endograft in an area other than at the location of the first staple, and advancing the staple of the second of the plurality of staplers from within the stapler housing such that the legs of the second staple form loops piercing the endograft and the vessel.

The loops may be closed loops.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof will be or become apparent to one with skill in the art upon reference to the following detailed description when read with the accompanying drawings. It is intended that any additional organizations, methods of operation, features, objects or advantages ascertained by one skilled in the art be included within this description, be within the scope of the present invention, and be protected by the accompanying claims.

In regard to the drawings.

FIG. 25 depicts a cut-away view of a stapler housing during a further step of firing the staple of FIG. 23a;

FIG. 26 depicts a cut-away view of a stapler housing during a still further step of firing the staple of FIG. 23a;

FIG. 27 depicts a cut-away view of a stapler housing during a still further step of firing the staple of FIG. 23a;

FIG. 28 depicts a cut-away view of a the staple of FIG. 23a fired into and endograft and an aortic wall;

FIG. 29a depicts a perspective view of a staple capable of being utilized with a stapler in accordance with a still further embodiment of the present invention;

FIG. 29b depicts a perspective view of the staple shown in FIG. 29a following firing by the endovascular stapler;

FIG. 31 depicts a cut-away view of a stapler housing during a further step of firing the staple of FIG. 29a;

FIG. 32 depicts a cut-away view of a stapler housing during a still further step of firing the staple of FIG. 29a;

DETAILED DESCRIPTION

Figure 1:
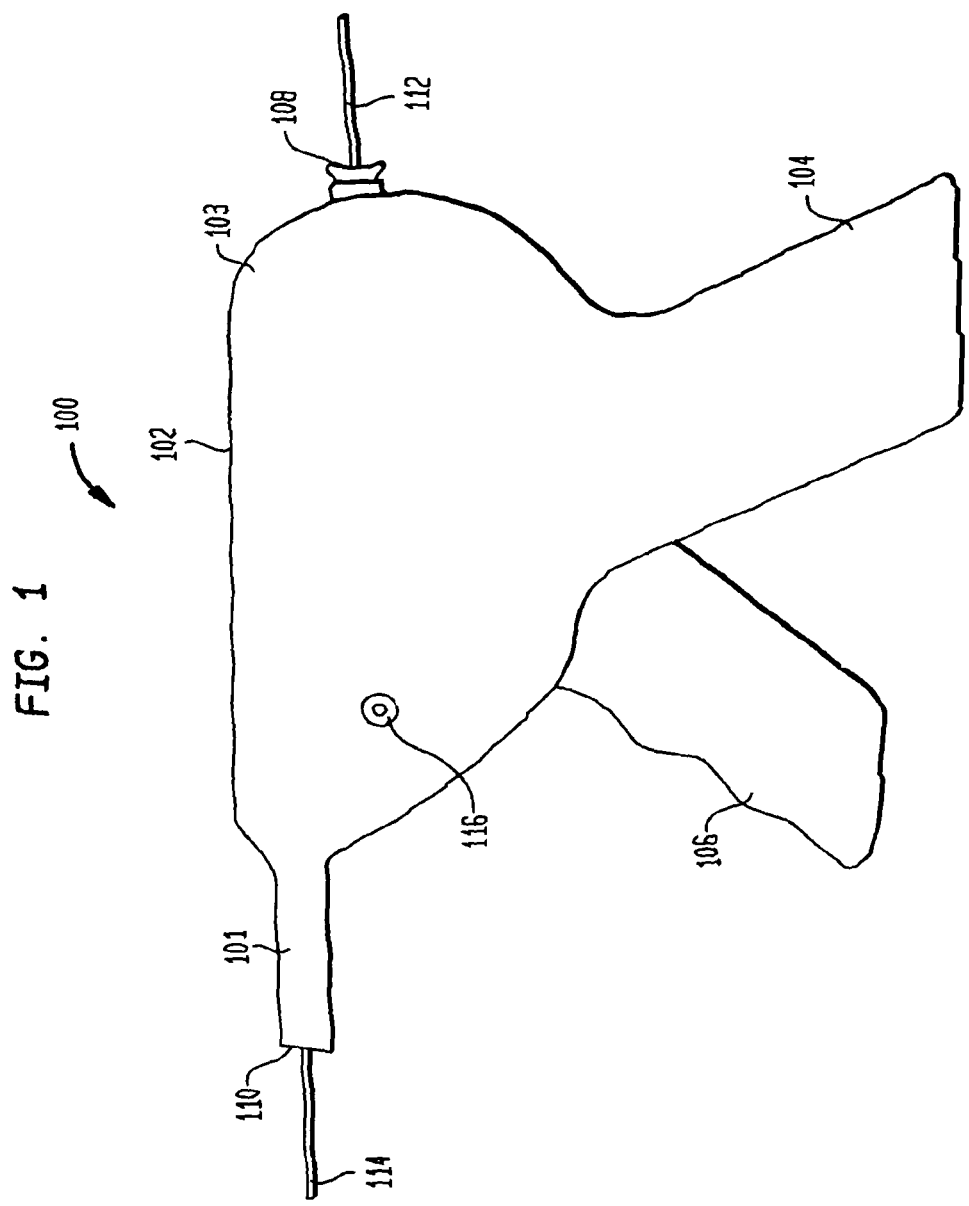
FIG. 1 is plan view of the handle portion of a stapler in accordance with one embodiment of the present invention.

In the following is described the preferred embodiments of the endovascular stapler of the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

In general, the endovascular stapler is a device which includes a stapling portion, or staple housing, intended to be inserted into the human body of a patient through an artery and apposed against a vessel wall, such as an aortic wall, or a graft. In order to maintain this position, a displacement device, such as a balloon, may be inflated near the stapling portion to push the stapling portion against the aortic wall or graft. Preferably, the displacement device is a noncompliant balloon. However, compliant balloons may also be utilized. Other displacement devices comprising webbed elements or multiple rods may also be utilized. A staple may then be advanced through the aortic wall and graft by actuating a trigger located on the body of the endovascular stapler, which remains outside of the patient's body. The staple may be either preformed with the some initial curvature or it may be flat. Either way, the stapling portion typically includes a conforming element to curve the staple as it advances. The staple will then penetrate the aortic wall and the graft and will curve in a predictable path such that its leading edge loops back, possibly repenetrating the exterior of the aortic wall and graft, thus holding the aortic wall and the graft against each other.

In embodiments where multiple staples may be inserted, the noncompliant balloon may be deflated and the stapler may be rotated to a second position, wherein another staple may be driven. The process may be repeated numerous times over the full 360° until a sufficient number of staples have been driven to adequately secure the graft to the aortic wall. Typically, this will entail driving up to eight staples.

In embodiments where the endovascular stapler houses only a single staple, the central portion of the stapler may be removed, reloaded and reinserted numerous times in order to drive multiple staples. Alternatively, several pre-loaded staplers may be provided. After discharging the staple from the first stapler, the stapler may be removed and discarded, wherein a second stapler may be inserted. This process may be repeated until a sufficient number of staples have been driven. Thus, the surgical staff will generally be ready with up to eight pre-loaded staplers per procedure, each stapler being utilized successively.

The endovascular stapler of the present invention may be an "over the wire" device designed to fit through a typical sheath for aortic and iliac arterial use, such as a 10 French sheath. It is also possible that the stapler may be miniaturized to fit through smaller sheaths for fixation of endografts in smaller caliber vessels.

In some embodiments, the stapler fires multiple staples sequentially. In such cases, the staples may consist of special precuts of alloy, such as Phynox, with sufficient column strength to be stacked in tandem within the staple channel and to be sequentially pushed therethrough. The staples must also be sufficiently pliable to easily track the curved internal staple guide, for some embodiments of the invention. In other embodiments, the staples must be loaded individually. In still further embodiments, the staples may be loaded automatically from a cartridge, but are not stacked in tandem. Rather, they may reside side-by-side in the cartridge.

The stapler is generally introduced through a groin sheath or other suitable access into the lumen of an endograft. Its leading elements are advanced to the proximal end of the endograft which should be accurately identified. Such identification may be by utilizing an ultrasonic probe. For future endografts, the ends of the graft fabric may be boldly marked with radio opaque thread. For older devices, radiologic techniques such as road mapping may be used to locate the ends of the graft. As is known in the art, multiple guide wires may be used during surgery.

When the stapling portion of the stapler is aligned with the proximal end of the endograft, the stapler head may be forcibly abutted against the endograft and vessel wall by inflation of a preferably noncompliant balloon. In this position, a single stroke of the stapler trigger preferably causes forward displacement of the staple pusher sufficient to advance a single staple through the graft and vessel wall.

In some embodiments, the curve of the staple guide causes the staple to form a circle or spiral, with a single piercing point on the leading portion of the staple. In other embodiments, the staple may form an exaggerated W. In this case, each end of the staple will pierce the endograft and the vessel wall as the staple is deformed by a staple détente.

In the case of an automatically loading stapler with staples aligned in tandem, the trigger of the stapler handle is then ratcheted back and cocked for the next firing. The specialized ratcheted design of this pusher and trigger is such that when fully cocked, a single trigger pull causes exactly the pusher excursion required to deploy the lead staple fully and bring the trailing staple segment into position at the tip of the curved staple guide for the firing of the next staple. For single staple designs, the stapler may be retracted and reloaded prior to the firing of a second staple. Alternately, additional staplers may be utilized during a single procedure, each firing only a single staple. Where multiple staples are fired from a cartridge holding staples side-by-side, the ratcheting mechanism of the trigger may include a feature permitting the pusher to be withdrawn back toward the body of the stapler, such that it is positioned for the firing of subsequent staples after the firing of a previous staple.

Inflation and deflation of the preferably noncompliant balloon may be performed manually or with any of the many available devices used for inflation and deflation of angioplasty balloons. A liquid such as dilute contrast or saline may also be used to distend the balloon.

Following each staple deployment, the balloon may be partially deflated, the stapler rotated, and the process repeated to deploy the next staple. For embodiments where staples are aligned in tandem, one limiting factor to the number of staples per device, and thus the length of the device, is the column strength of the staple alloy as the staples aligned in a row are each driven by the trailing staples, and ultimately by the excursion of the staple pusher. It will be readily apparent that the staples should be of sufficient column strength so as not to become deformed within the stapler prior to being applied. It will also be apparent that a single staple may be required to push several proceeding staples.

In embodiments where the staples are stored in tandem, the staples may be cut such that the diamond shaped tip of each trailing staple fits into a diamond shaped cavity formed at the end of each leading staple. For devices employing a single staple or employing a cartridge of side-by-side staples, the column strength of the individual staple is less of a concern. Of course, it should be sufficient to adequately secure the stent graft, however. In other embodiments, the individual staples may each be pushed by individual staple pushers.

Referring to the figures, FIG. 1 depicts an endovascular stapler 100 in accordance with one embodiment of the present invention. As is shown, the stapler 100 may generally be shaped like a gun. The stapler 100 may comprise a housing 102 having a handle 104 and a trigger 106 extending therefrom. The housing may also include a barrel 101 having an output aperture 110. An input boss 108 may be located at the rear 103 of the housing 102. A guide wire 112 may extend into the input boss. Extending from the output aperture 110 may be a staple housing 114. The stapler 100 may also include a balloon inflation port 116.

Figure 2:
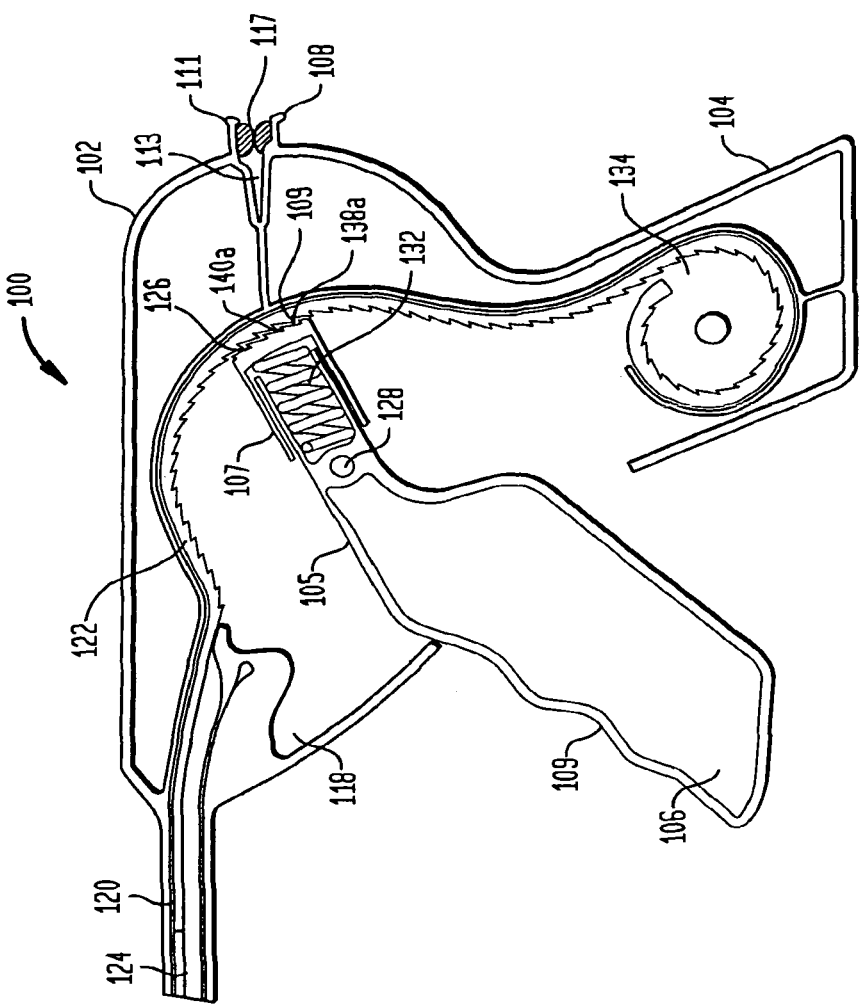
FIG. 2 is a sectional view of the stapler of FIG. 1 showing the internal components thereof.

FIG. 2 depicts a cut-away view of the stapler 100 of FIG. 1. As shown, the trigger 106 may comprise an inner section 105 and an outer section 107. The inner section 15 may also include a grip 109, exterior to the housing 102. The inner section 105 may include a pin 128 attaching the trigger 106 to the housing 102, and about which the trigger may rotate. The trigger 106 may also include a spring mechanism (not shown) to bias the trigger 106 away from the handle 104. The outer section 107 of the trigger 106 may be attached to the inner section by a spring 132. Advantageously, the outer section 107 is permitted to shift relative to the inner section 105, to compress the spring 132. A toothed element 126 of the outer section 107 includes teeth 109 having sloped sections 138 and edges, or lips 140. Each of the sloped sections 138 of the teeth 109 assist with ratcheting action of the trigger 106, as will be discussed hereinafter.

A ratcheted stapler pusher 120 may curve between the trigger 106 and a path created by the internal cavity 118 formed from the housing 102. The pusher 120 may include a ratcheted portion 122 at its trailing portion and a cylindrical portion 124 at its leading portion. The ratcheted portion 122 includes sloped sections 138 which may engage the toothed elements 126 of the stapler trigger 106. Upon actuation of the stapler trigger 106, which initiates rotation of the toothed elements 126 about pin 128, the pusher 120 may be displaced through the barrel 101 toward the distal end 130 (FIG. 4) of the stapler 100. As the trigger 106 is returned to its initial position, spring 132 permits ratcheting of the toothed elements 126 such that the pusher 120 remains in this advanced position. Portions of the ratcheted portion 122 of the pusher 120 may be stored in a spiral configuration within staging area 134, located within the handle 104 of the stapler 100.

Also shown in FIG. 2 are the internal components of the input boss 108. The input boss 108 comprises a flange 111 formed from the housing 102. The flange includes a cavity 113 extending into the internal cavity 118 of the housing 102. Within the cavity 113 near the flange 111 may be a pair of rubberized elements 115 having a boundary 117 therebetween. The guide wire 112 (FIG. 1) may be permitted to pass along this boundary from the exterior of the housing 102 to the internal cavity 118. Once inside the internal cavity 118, the guide wire may be permitted to extend through the barrel 101 into the guide wire channel 144 (FIG. 4) of the staple housing 114, as will be discussed.

Figure 3:
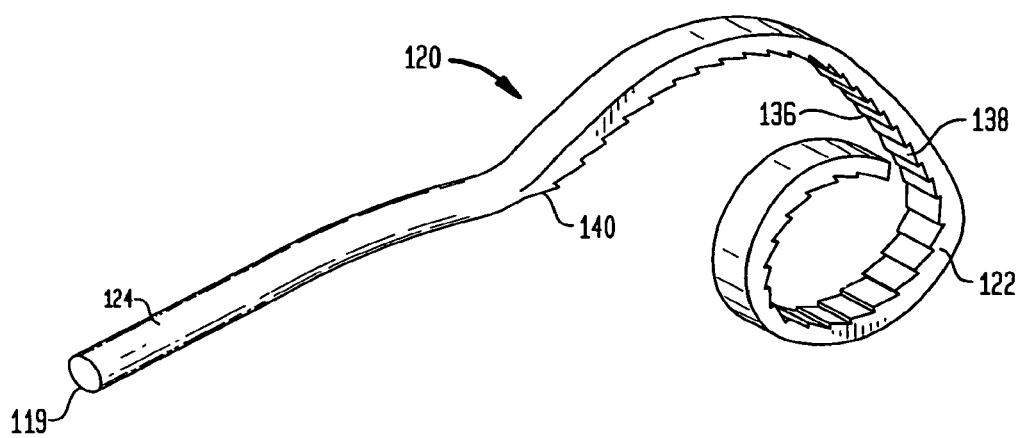
FIG. 3 is a perspective view of a pusher forming a portion of the stapler of FIG. 1.

FIG. 3 depicts a perspective view of the pusher 120. This figure clearly depicts the cylindrical portion 124 at the front of the pusher 120 and the ratcheted portion 122 at the rear of the pusher. The ratcheted portion 122 may comprise a series of ramps 136 having sloped sections 138 ending in lips 140. As discussed, the toothed element 126 of the stapler trigger 106 incorporates teeth 109 which may be sized and configured similarly to the sloped sections 138. The engagement of each of these elements facilitates displacement of the pusher 120 when the trigger 106 is activated, but permits ratcheting of the trigger upon the return stroke.

Also shown in FIG. 3 is the front face 119 of pusher 120. As will be discussed, the front face 119 of the pusher may be adapted to contact and advance a series of staples 148 (FIG. 4).

Figure 4:
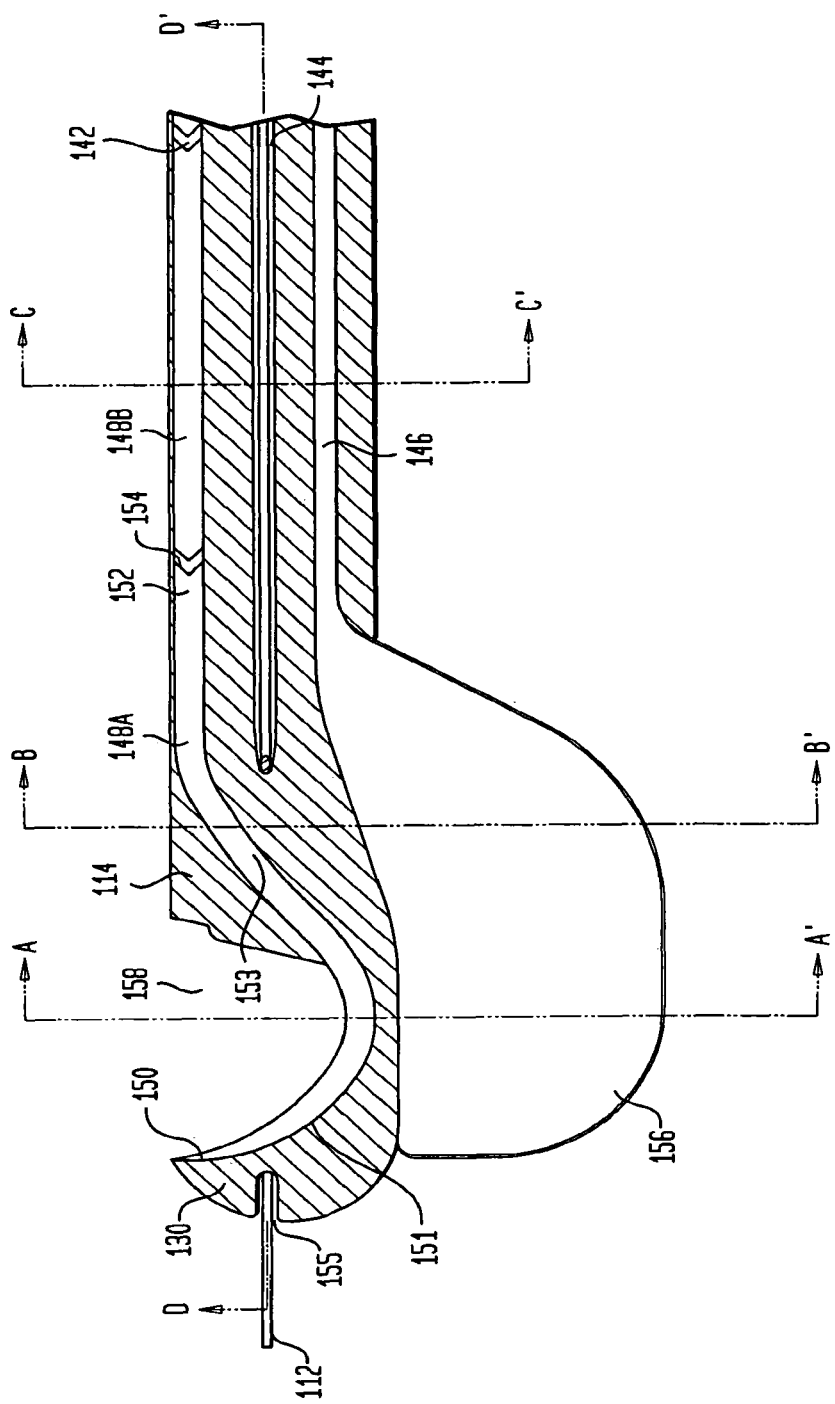
FIG. 4 is a longitudinal sectional view of the distal end of the staple housing forming a portion of the stapler of FIG. 1 showing the internal components thereof.

FIG. 4 depicts a longitudinal sectional view of the distal end 130 of the staple housing 114. As shown, the staple housing 114 may incorporate a staple channel 142, a guide wire channel 144, and a balloon inflation channel 146. Each of the channels may be generally cylindrical and typically run the entire length of the staple housing 114 from the outlet aperture 110 of the housing 102 to the distal end 130 of the staple channel 146.

The staple channel 142 typically houses a series of staples 148 placed consecutively in tandem including a first staple 148a and a second staple 148b. Preferably, each staple has a pointed proximal end 150 and a distal end 152 with a cavity 154 or recess matching the pointed proximal end. The cavity of the leading staple, such as the first staple 148a, therefore may be filled by the pointed proximal end 150 of the subsequent staple, such as the second staple 148b.

As will be discussed, the stapler 100 is generally employed to fire a multiplicity of staples 148 sequentially to secure a graft to a vessel. The staples 148 preferably consist of special precuts of alloy, such as Phynox, with sufficient column strength to be placed in tandem within the staple channel 142 so as to be pushed ahead by the trailing staples. Each of the staples 148 is also preferably sufficiently pliable to easily track the curved internal staple guide 151.

For example, the first staple 148*a* may be pushed by the second staple 148*b*, as well as the subsequent staples, by the pusher 120 upon actuation of the trigger 106. As the first staple travels along the staple channel 142, it will begin to be bent by a bending portion 153 of the staple channel 142, toward the distal end 130 of the staple housing 114. It will be appreciated that the bending portion 153 of the staple housing curves such that the staple 148 exiting the bending portion will be pre-curved as it enters the internal staple guide 151. As will be discussed hereinafter, as the staple 148 passes the staple guide 151, it will continue to be shaped such that the staple will form a loop capable of penetrating each of a graft and a vessel in at least two locations.

The guide wire channel 144 extends along the entire length of the staple housing 114 parallel and adjacent to the staple channel 142. The guide wire channel provides a housing for the guide wire 112, which is used to advance the distal end 130 of the stapler 100 to the location where the stapling is to be conducted.

Generally, advancement of the endovascular stapler 100 is considered to be via an "over the wire" type system. As an "over the wire" device, the staple housing 114 portion of the stapler 100 is designed to be guided through vessels following the path of a previously installed guide wire 112. For example, a guide wire 112 may be placed in an artery in a surgical procedure. The distal end 130 of the staple housing 114 may then be pushed along the length of the guide wire 112, which travels from a guide wire exit point 155 at the distal end 130, through the guide wire channel 144 and out the input boss 108 of the housing 102. Once the distal end 130 reaches its destination, advancement may cease and the stapler 100 is ready deploy a staple 148. It will be appreciated that the staple housing 114 may be constructed of flexible materials such that it may bend as necessary along the path toward the area in which a staple 148 is to be deployed.

Preferably, the endovascular stapler of the present invention is designed to fit through a 10 French sheath or 16 French sheath for aortic and iliac arterial use. However, it is also foreseeable that the stapler may be miniaturized to fit through smaller sheaths for fixation of endografts in smaller caliber vessels. Where deemed appropriate, larger sheaths may also be utilized.

Also shown in FIG. 4 is the balloon inflation channel 146 of the staple housing 114. Extending from the balloon inflation channel 146 is a noncompliant balloon 156. In the view shown in FIG. 4, it will be appreciated that the noncompliant balloon 156 is shown inflated. In a deflated condition, the noncompliant balloon is generally quite thin, and typically fits neatly against the balloon inflation channel 146.

The noncompliant balloon 156 may be inflated prior to the firing of a staple 148. One purpose of inflating the noncompliant balloon 156 is to force the staple exit area 158 of the staple housing 114 against the area where the staple 148 is to be fired. This not only places the staple 148 immediately adjacent to the receiving area, but it assists with preventing the staple housing 114 from being moved, linearly or rotationally, during the firing of the staple 148.

Selective inflation and deflation of the noncompliant balloon 156 is completed through the balloon inflation port 116 of the housing 102. It will be appreciated that the balloon inflation port 116 may include a valve (not shown) upon which a liquid source (not shown) may be attached. The liquid source may be permitted to flow into the balloon inflation port 116 to inflate the noncompliant balloon 156. Deflation of the noncompliant balloon 156 may be accomplished at the balloon inflation port 116 by releasing liquid therefrom, such as by opening the valve or by sucking liquid out of the noncompliant balloon 156 through use of the liquid source, which may have the capability of reversing direction of flow to form a vacuum. It will be appreciated that the balloon inflation port 116 is in fluid communication with the noncompliant balloon 156 via the balloon inflation channel 146. Inflation and deflation may also be conducted with any of the available devices used for inflation and deflation of angioplasty balloons. Typically, the liquid used for inflating and deflating the balloon will be dilute contrast or saline.

Upon firing of the staple 148, the noncompliant balloon 156 may then be deflated so the staple housing 114 may be rotated to a second position in preparation for the firing of a second staple 148. Prior to firing the second staple 148, the noncompliant balloon 156 may be re-inflated to place the staple exit area 158 of the stapler 100 in position in preparation for firing.

Figure 5:
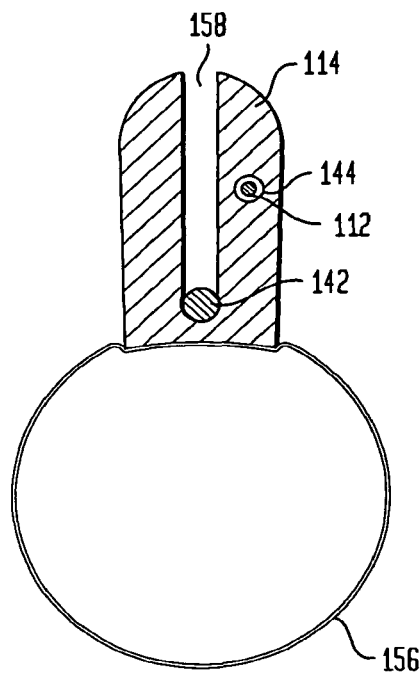
FIG. 5 is a cross-sectional view of the distal end of the staple housing shown in FIG. 4 taken along section lines A-A.

FIG. 5 depicts a cross sectional view of the staple housing 114 taken along section line A-A of FIG. 4. As with FIG. 4, the noncompliant balloon 156 is shown inflated. As shown in FIG. 5, the guide wire channel 144 may be offset within the staple housing 114 around the staple exit area 158 (also shown in FIG. 4). This offset allows for the formation of the curved area 153 of the staple channel 142, as well as the staple guide 151 along the longitudinal centerline of the staple housing 114.

Figure 6:
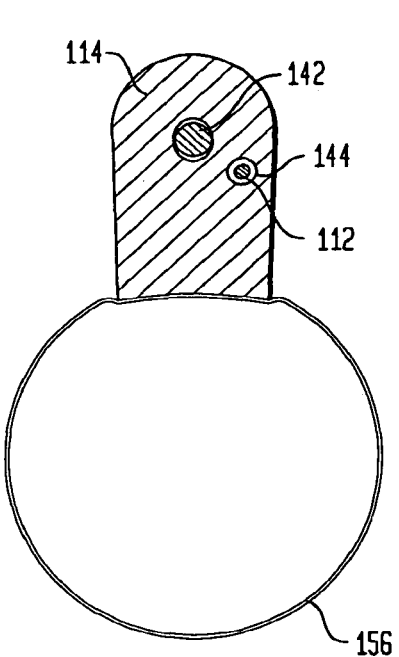
FIG. 6 is a cross-sectional view of the distal end of the staple housing shown in FIG. 4 taken along section lines B-B.

FIG. 6 depicts a cross sectional view of the staple housing 114 taken along section line B-B of FIG. 4. As shown in FIG. 4, section line B-B is taken closer to the housing 102 than section line A-A. In this cross-section, the staple exit area 158 is not yet visible. Yet, a staple 148 within the staple channel 142 and the guide wire 112 within the guide wire channel 144 clearly are. In addition, the noncompliant balloon 156 is shown in the inflated condition.

Figure 7:
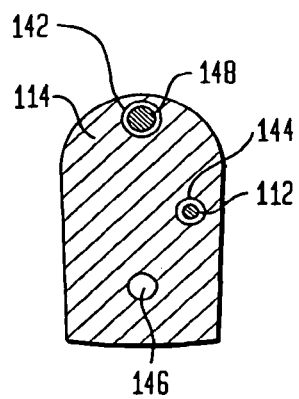
FIG. 7 is a cross-sectional view of the distal end of the staple housing shown in FIG. 4 taken along section lines C-C.

FIG. 7 depicts a cross sectional view of the staple housing 114 taken along section line C-C of FIG. 4. In this upstream section, it is clearly shown that the stapled channel 142, guide wire channel 144 and balloon inflation channel 146 may all be stacked on a single vertical axis within the staple housing 114. This orientation constitutes the orientation of the various channels 142, 144, 146 for most of the length of the staple housing 114.

Figure 8:
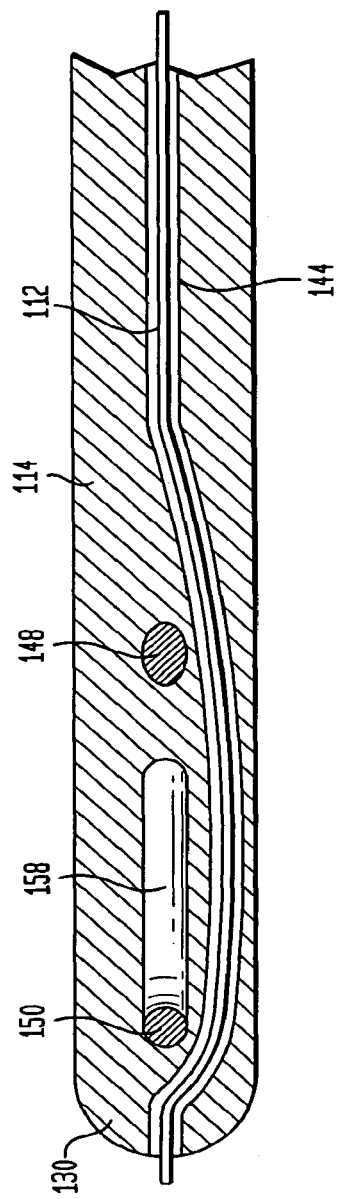
FIG. 8 is a longitudinal section of the distal end of the staple housing shown in FIG. 4 taken along section lines D-D.

FIG. 8 depicts a longitudinal section view of the distal end 130 of staple housing 114 shown in FIG. 4 taken along section lines D-D. In this view, the staple exit area 158 is clearly depicted with the proximal end 150 of the staple 148 nearest the distal end 130 of the staple housing 114. Also shown in the guide wire channel 144 with the guide wire 112 offset to permit formation of the staple exit area 158.

Figure 9:
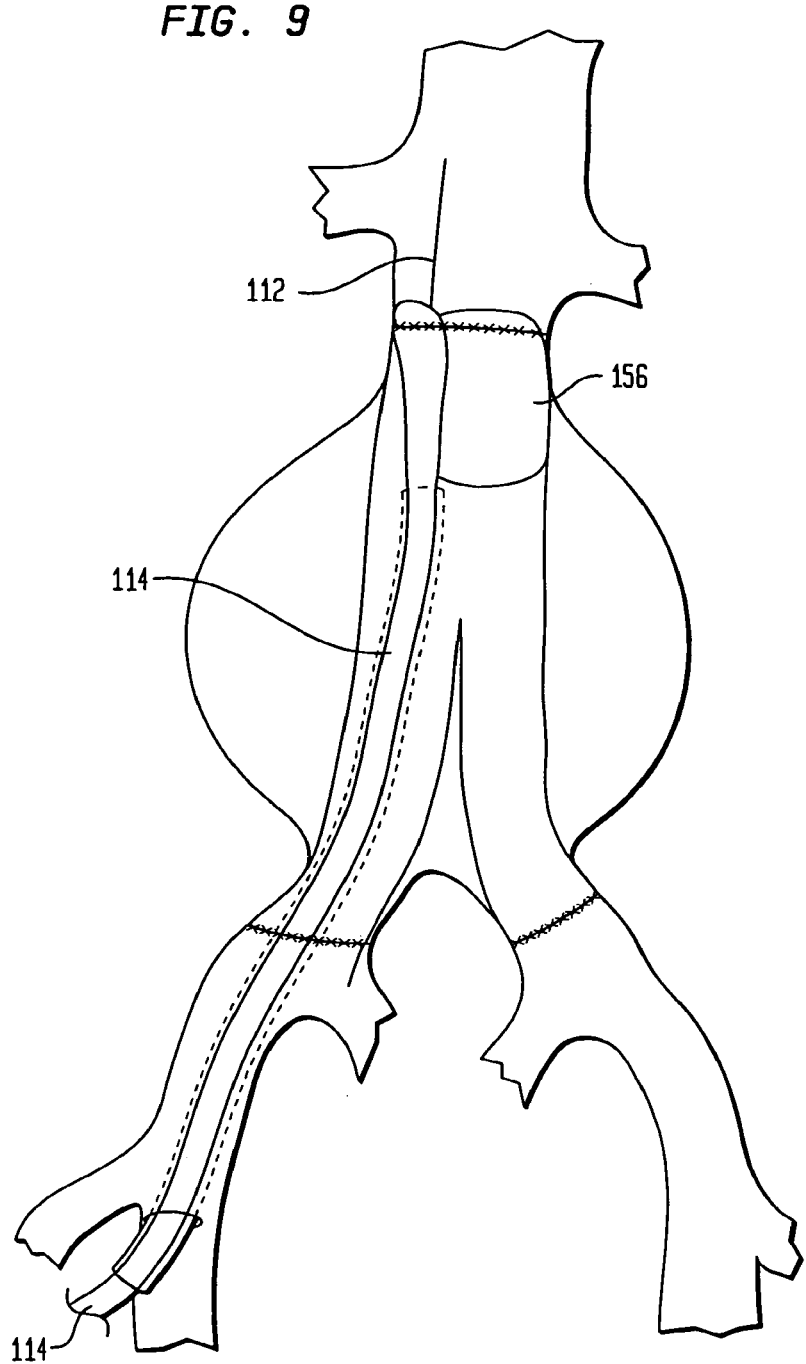
FIG. 9 is a cut-away view of the abdominal cavity of a patient depicting the general orientation of the staple housing forming a portion of the stapler utilized in a method of arresting graft migration in accordance with one embodiment of the present invention.

FIG. 9 depicts a staple housing 114 inserted into a sheath within the human body. The staple housing 114 is typically introduced into the groin or other suitable access area where it follows the previously inserted guide wire 112 into the lumen of the endograft to be sutured. Also shown in FIG. 9 is the noncompliant balloon 156 in a fully inflated condition. As previously discussed, the distal end 130 of the staple housing 114 will be pushed against the aortic sidewall by the noncompliant balloon 156. When so pushed, a first staple 148*a* may be fired. Subsequent staples 148 may be fired after deflation of the noncompliant balloon 156, rotation of the staple housing 114 and inflation of the noncompliant balloon such that the staple exit area 158 is aligned at the intended deployment location.

Figure 10:
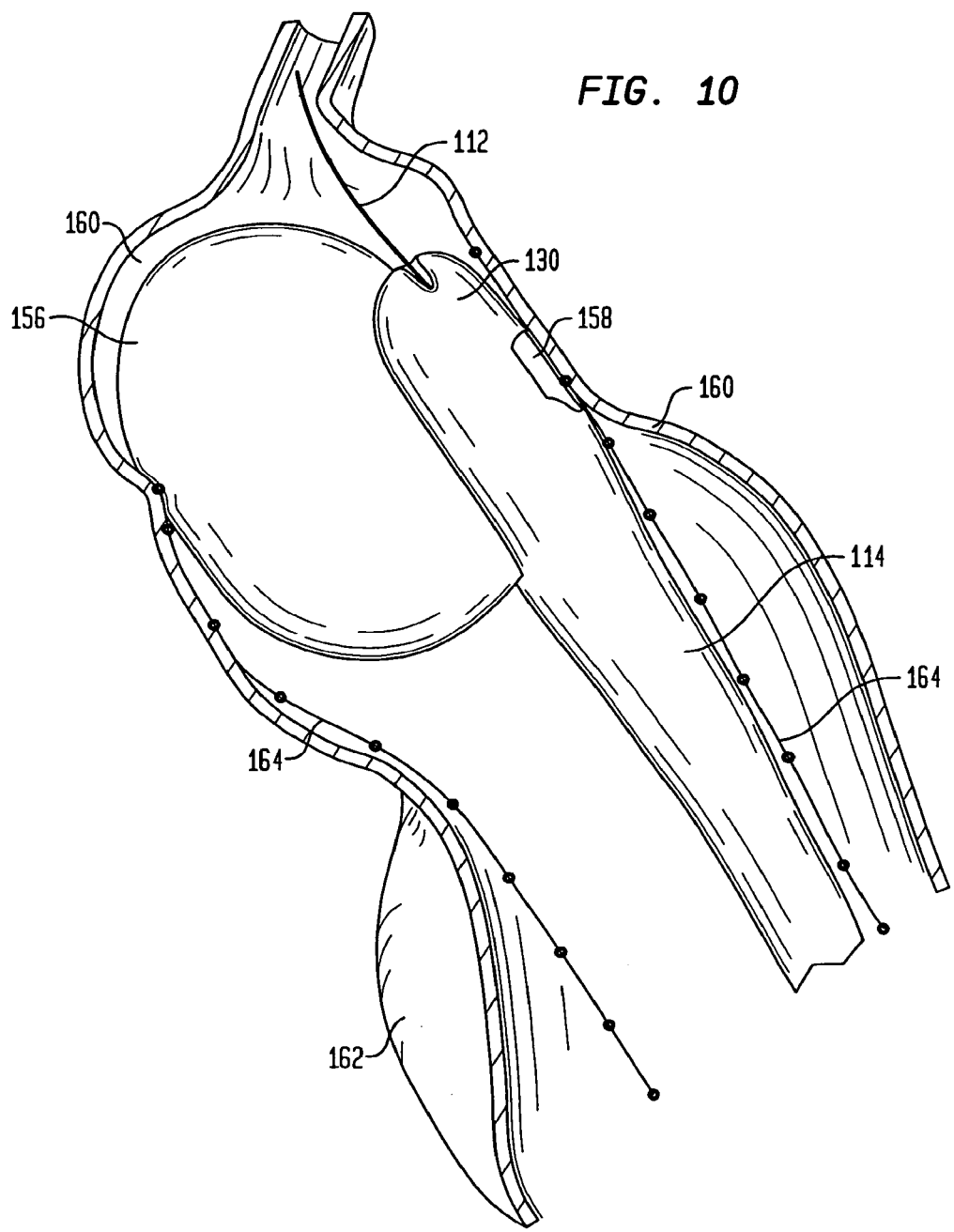
FIG. 10 is a second cut-away view of the abdominal cavity of a patient depicting the general orientation of the staple housing forming a portion of the stapler utilized in the method of arresting graft migration in accordance with one embodiment of the present invention.

FIG. 10 depicts a close-up cut-away view of the distal end 130 of the endovascular stapler 100 in use. As discussed, the distal end 130 of the stapler 100 may be inserted into the aorta 160 through a sheath (not shown) along a guide wire 112. The proximal end 130 may then be positioned so as to cover the aortic aneurysm 162 intended to be cured. As previously discussed, the noncompliant balloon 156 may then be enlarged such that the staple exit area 158 of the stapler 100 will be pushed up against the endograft 164 and the aortic sidewall 160, as shown in FIG. 10.

Figure 11:
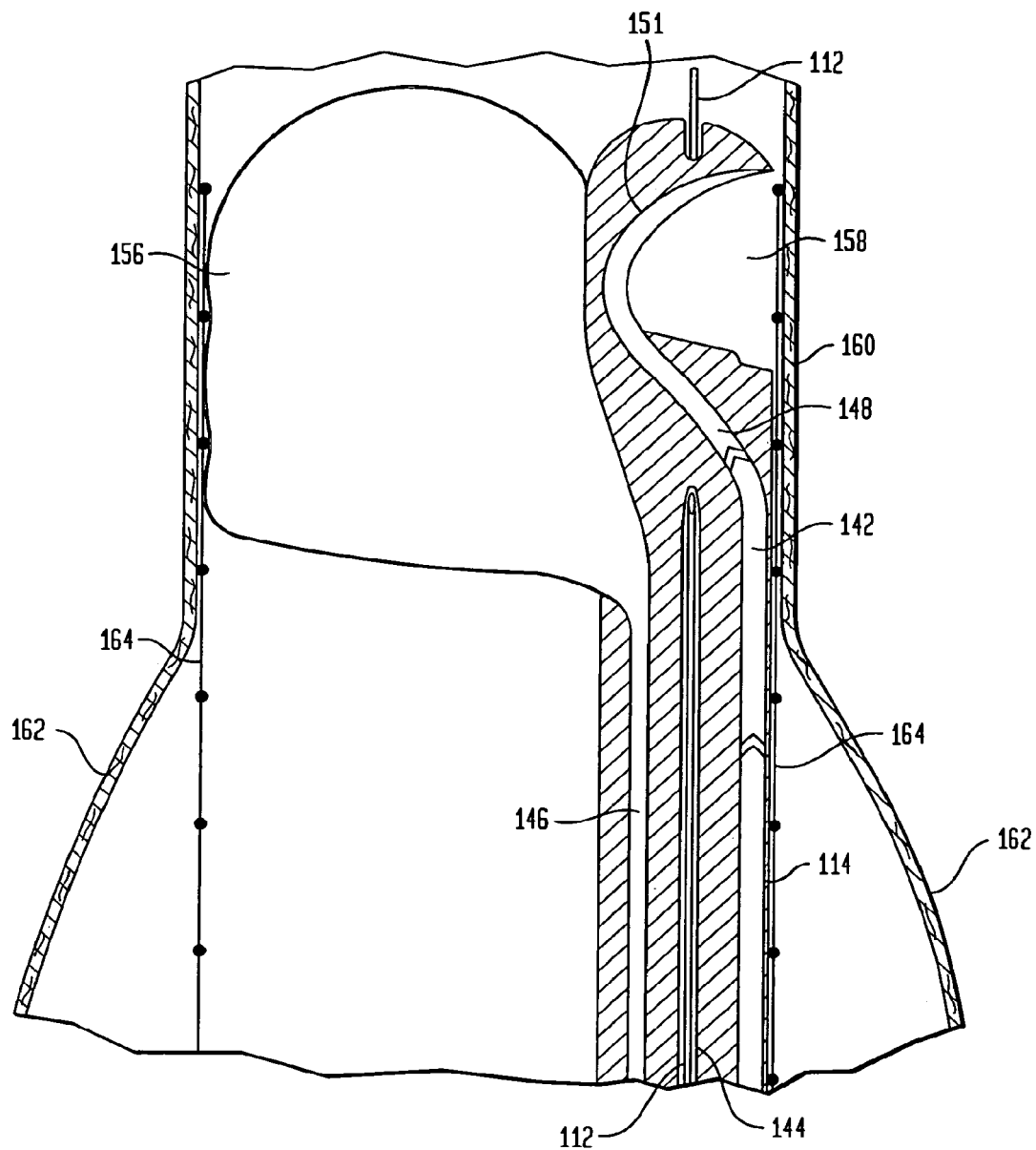
FIG. 11 is a cut-away view of the abdominal cavity of a patient depicting an initial step of the method of affixing a graft into an aortic aneurysm in accordance with one embodiment of the present invention.

FIG. 11 depicts a longitudinal section view of this arrangement showing the internal components of the staple housing 114. In this view, it is clearly shown that the first staple 148a is being pushed by the second staple 148b through the curved area 153 of the staple channel 142. Such curvature of the staple channel deforms the first staple 148a permitting the staple to curve around the curved internal staple guide 151 toward the staple exit area 158. Again, the staple exit area 158 is shown adjacent to the area in which the staple 148 is to be deployed. Secure placement of the staple exit area 158 is achieved via inflation of the noncompliant balloon 156.

Figure 12:
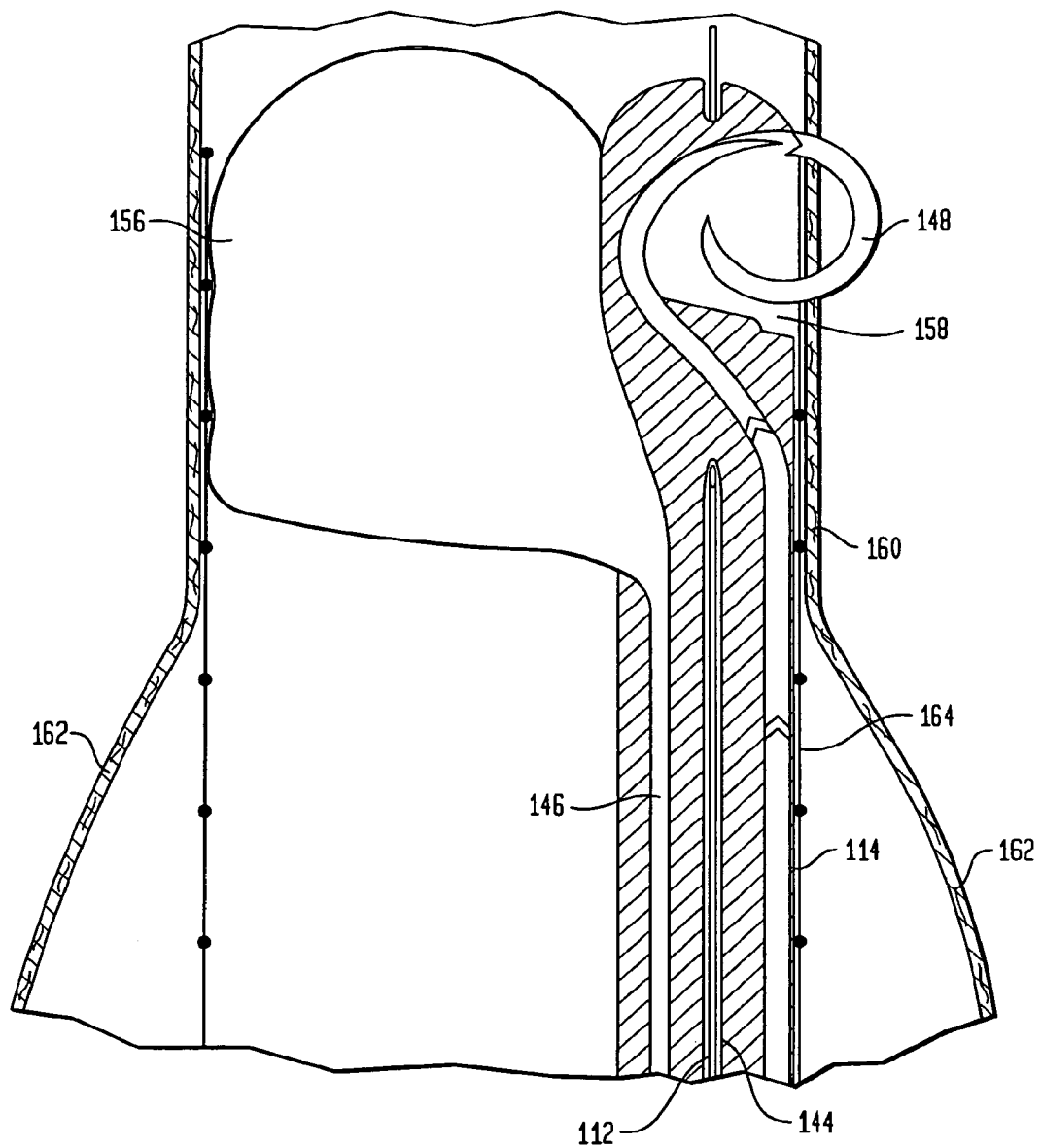
FIG. 12 is a cut-away view of the abdominal cavity of a patient depicting a further step of the method of affixing a graft into an aortic aneurysm of FIG. 11.

FIG. 12 depicts the longitudinal section view of FIG. 11 after the firing of a staple 148. As shown, internal staple guide 151 has formed the staple 148 into a ring or loop engaging the endograft 164 and the aortic sidewall 160 from the interior of the aorta 160 and then returning back around to again engage the aortic sidewall 160 and the endograft 164 from the exterior of the aorta. As previously discussed, the noncompliant balloon 156 may then be temporarily deflated such that the staple housing 114 may be rotated and placed in a position for the firing of a second staple 148b.

The stapler is typically introduced into the patient through a groin sheath or other suitable access into the lumen of the endograft. It is advanced to the proximal end of the endograft which should be accurately identified. For future endografts, the ends of the graft fabric is boldly marked with radio opaque thread. For older devices, radiologic techniques such as road mapping may be used to locate the ends of the graft. As is known in the art, multiple guide wires may be used during surgery.

As will be discussed, the staples may be driven in the direction of blood flow or against the direction of blood flow, depending on the embodiment of endovascular stapler utilized. These two directions may depend on the configuration of the particular staple utilized, as will be discussed. Other factors may also contribute to the determination of an installment direction.

When the stapling end of the stapler is aligned with the end of the endograft, the stapler head is forcibly abutted against the endograft and vessel wall by inflation of a balloon. In this position, pulling of the stapler trigger causes forward displacement of the staple pusher sufficient to advance a single staple through the graft and vessel wall. The curve of the staple guide causes the staple to form a circle. The trigger of the stapler handle is then cocked for the next firing. The specialized ratcheted design of this pusher and trigger is such that when fully cocked, the trigger pull causes exactly the pusher excursion needed to deploy the lead staple fully and bring the trailing staple segment into position at the tip of the curved staple guide.

Inflation of the preferably noncompliant balloon may be performed manually or with any of the many available devices used for inflation of angioplasty balloons. A liquid such as dilute contrast or saline may be used to distend the balloon.

Following each staple deployment, the balloon is deflated, the stapler is rotated and the process is repeated to deploy the next staple. The only limiting factor to the number of staples per device, and thus the length of the device, is the column strength of the staple alloy as the staples aligned in a row are driven each by the trailing staple and ultimately by the excursion of the staple pusher.

The staples may be cut such that the diamond shaped tip of the trailing staple fits into the diamond shaped cavity formed at the end of the lead staple. In other embodiments, individual staple pushers may push each staple.

Figure 14:
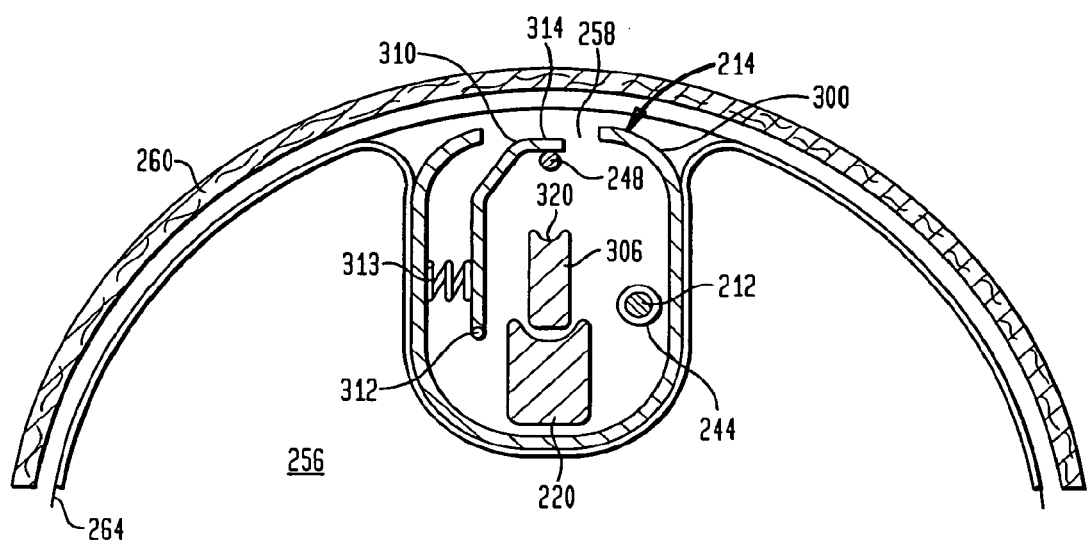
FIG. 14 depicts a cross-sectional view of the distal end of the staple housing of the stapler in accordance with the second embodiment of the present invention in an initial position.

FIG. 14 depicts a cross-sectional view of a portion of the staple housing 214 of an endovascular stapler (not shown) in accordance with a second embodiment of the present invention. In this embodiment, a single staple 248, formed in the shape of an elongated W may be applied to secure a graft 264 against a vessel, shown in FIG. 14 as an aortic wall 260. Typically, the chief function of a stapler in accordance with this embodiment is for use to arrest device migration of a previously placed endograft. Other embodiments employing multiple elongated W-shaped staples may also be used to arrest device migration of a previously implanted endograft or to affix a new endograft. Still further embodiments permit the withdrawal of portions of the stapler which may then be replaced with other portions pre-loaded with a staple for a subsequent firing.

Figure 13:
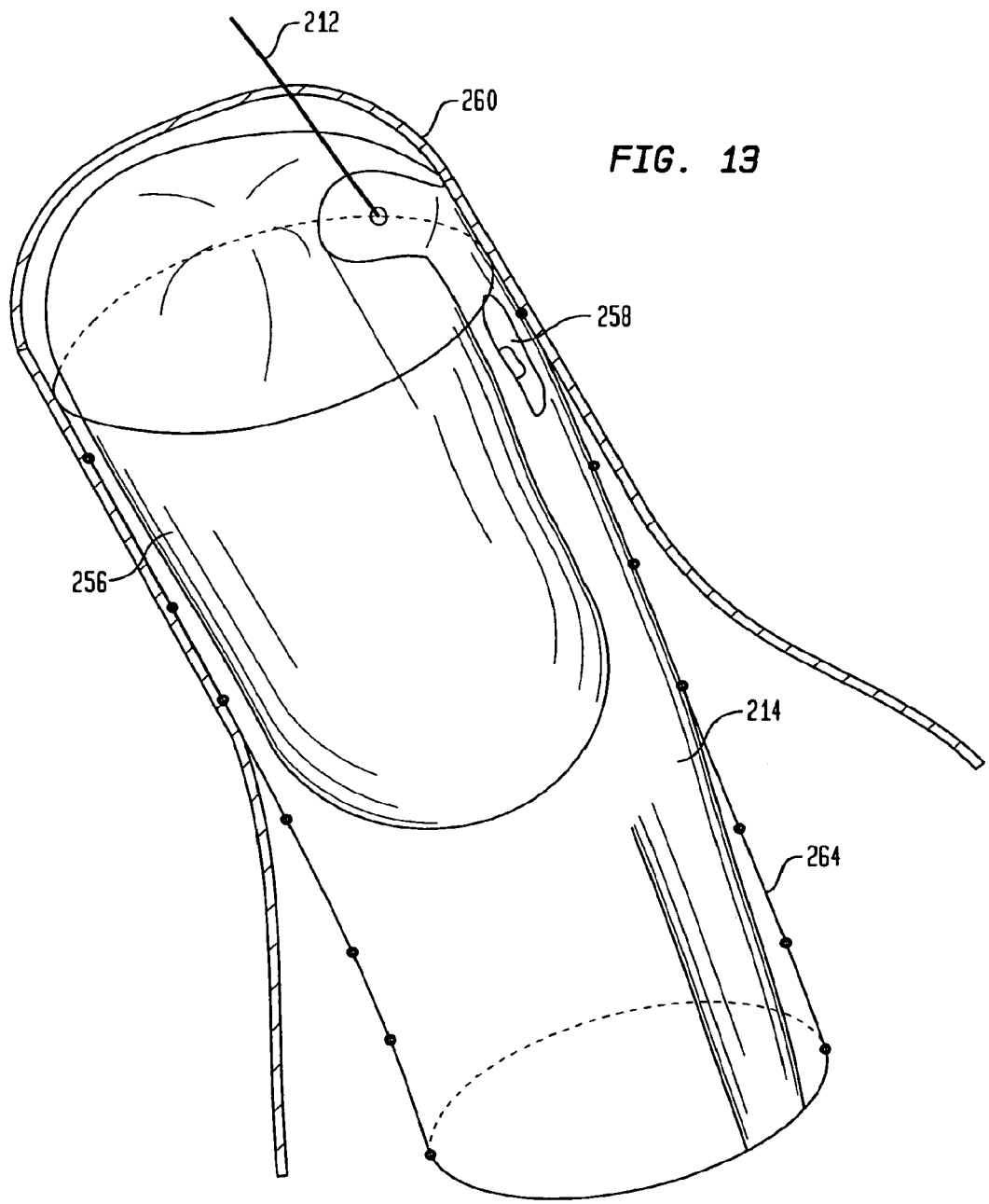
FIG. 13 is a sectional view of a portion of an endovascular stapler in accordance with a second embodiment of the present invention inserted into an aortic wall.

FIG. 13 depicts a partially cut-away perspective view of a stapler housing 214 and a noncompliant balloon 256 inserted within an aortic wall 260 in preparation for attachment of a stent graft 264. As shown in FIG. 13, the stapler housing 214 may be placed into position by being strung along a guide wire 212 in an "over the wire" type system, as previously discussed. Once positioned properly, such that the staple exit area 258 is adjacent to the intended deployment area, the noncompliant balloon 256 may be inflated, as shown in FIG. 13, to push the staple exit area against the stent graft 264, which in turn is pushed against the aortic wall 260. The staple 248 may then be fired and the stapler housing 214 removed. Firing of the staple 248 may be achieved utilizing a housing with a ratcheted trigger, as with other embodiments of the invention.

Figure 15:
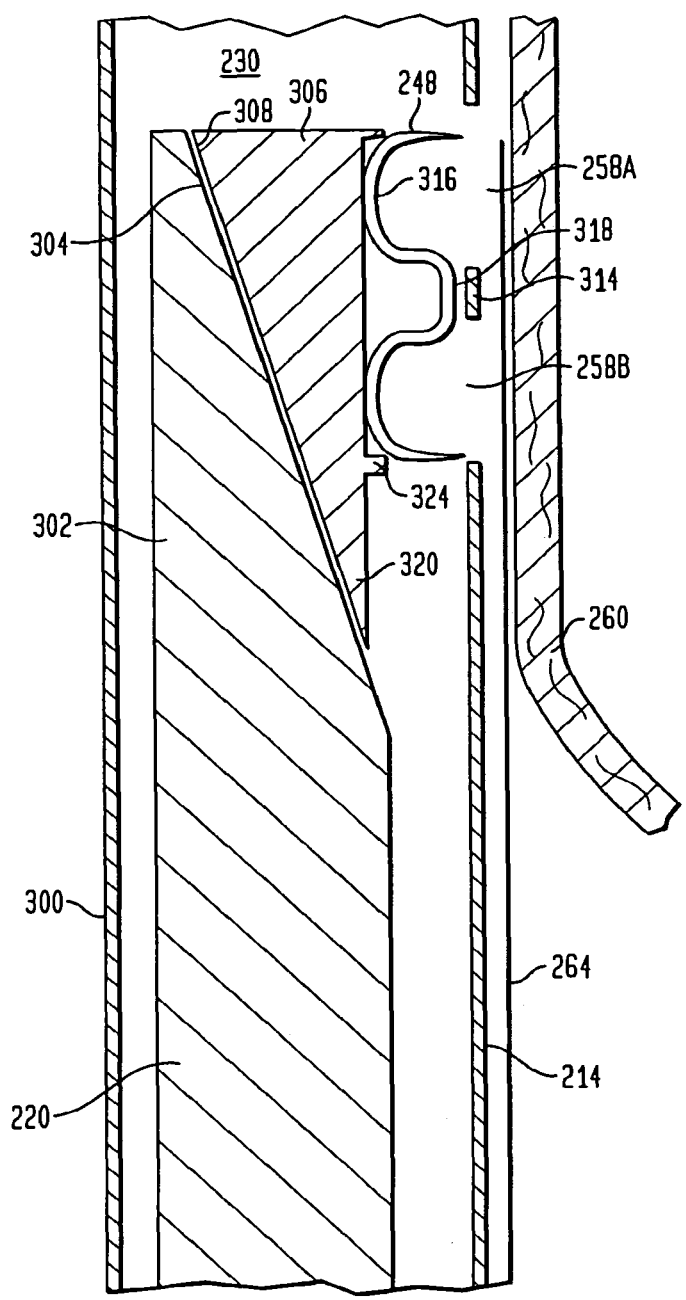
FIG. 15 depicts a longitudinal section view of the distal end of the staple housing of the stapler in accordance with the second embodiment of the present invention in the initial position shown in FIG. 14.

As shown in FIG. 14, the staple housing 214 may include an exterior casing 300 having a staple exit area 258 at its distal end 230 (FIG. 15). A pusher 220 may extend the full length of the exterior casing 300, from stapler to the staple exit area 258. As shown in FIG. 15, the pusher 220 includes a tapered section 302 adjacent the staple exit area 258. The tapered section 302 includes an inclined surface 304. Adjacent the inclined surface 304 is an actuator 306. The actuator 306 includes an inclined surface 308 adjacent the inclined surface 304 of the tapered section 302.

Referring back to FIG. 14, there is shown a staple détente 310 shown within the exterior casing 300. Although not shown in the figures, the stapler détente 310 is connected at one end to the exterior housing 300 by a rotatable connection, such as a hinge 312 mounted to the housing or to protruding portions of the housing. Two such protruding portions may also support a rod about which the détente 310 may be rotated and to which the détente 310 may be connected. The rod may span the protruding portions or may be connected to them at internal intervals of the rod.

The second end 314 of the staple détente 310 may extend toward the staple exit area 258, to divide the staple exit area into a first staple exit area 258A and a second staple exit area 258B, as shown in FIG. 15. A spring 313 may be mounted between the exterior casing 300 and the staple détente 310 such that the détente is biased into the position shown in FIG. 14, where the spring is shown in its fully extended position. As will be discussed, the détente 310 may be rotated from this position upon application of a compressive force upon the spring 313.

As with the first embodiment, a guide wire channel 244 is also located within the staple housing 214. The guide wire channel 244 permits the use of a guide wire 212 in an "over the wire" system, to properly place the staple exit area 258.

FIG. 14 also depicts a portion of a noncompliant balloon 256. The noncompliant balloon 256 of the second embodiment may be completely exterior of the staple housing 214. The noncompliant balloon 256 is intended to be inflated such that the staple housing 214 will be pushed against the stent graft 264 such that the stent graft may be firmly apposed against the aortic wall 260.

Also included within the staple housing 214 is an elongated W-shaped staple 248. As shown in FIG. 15, the staple 248 includes two U-shaped sections 316 connected by a bridge 318. Each of the U-shaped sections 316 of the staple 248 sits against the front surface 320 of the actuator 306. At the extreme ends of the staple 248, the front surface 320 extends out to form flanges 324 which act to capture the staple and secure it in place. In addition, the front surface 320 of the actuator is curved, as shown in FIG. 14, to assist with securing the staple 248 in place.

Figure 16:
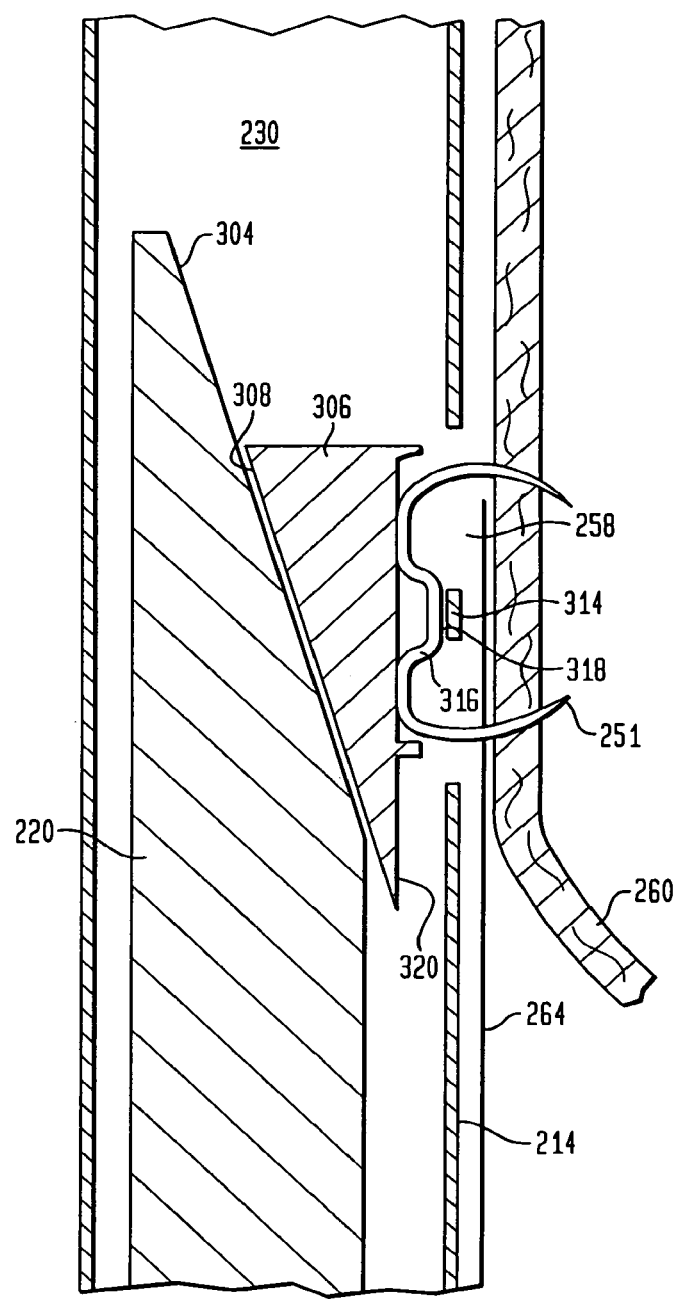
FIG. 16 depicts a longitudinal section view of the distal end of the staple housing of the stapler in accordance with the second embodiment of the present invention in an advanced position.
Figure 17:
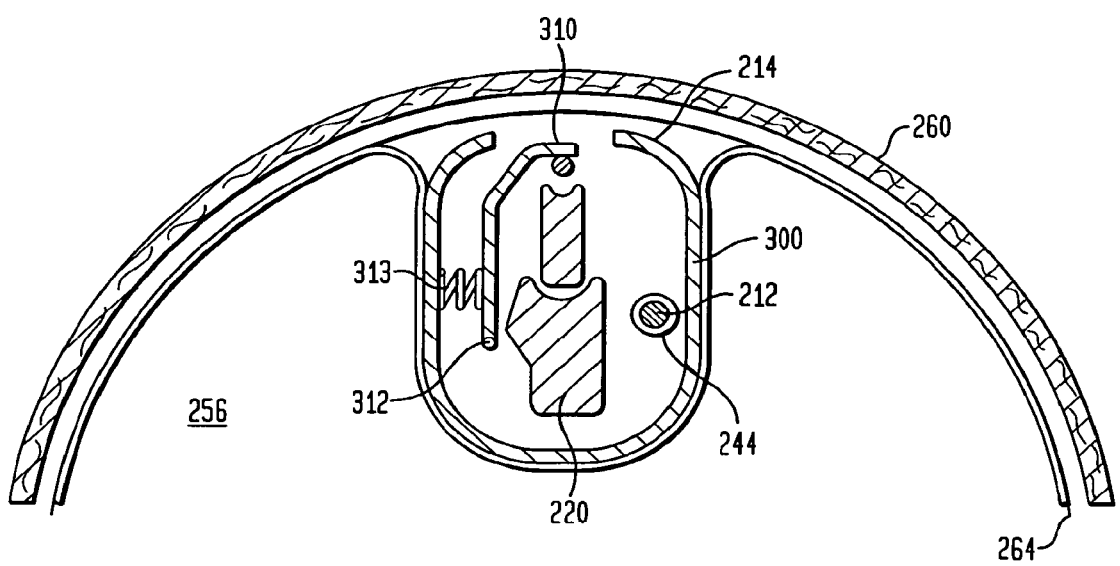
FIG. 17 depicts a cross-sectional view of the distal end of the staple housing of the stapler in accordance with the second embodiment of the present invention in the advanced position shown in FIG. 16.

As the trigger of the stapler is actuated, the ratcheted stapler pusher 220 is advanced toward the distal end 230 of the staple housing 214. As shown in FIG. 16, advancement of the pusher 220 toward the distal end 230 of the staple housing 214 causes the inclined surface 304 of the pusher to contact the inclined surface 308 of the actuator 306. As the pusher 220 is advanced, the front surface 320 of the actuator 306 will be pushed perpendicularly toward the staple exit area 258 due to the interaction between the inclined surfaces 304, 308. Advancement of the actuator 306 will push the bridge 318 of the staple 248 against the second end 314 of the staple détente 310, as shown in FIGS. 16 and 17. This advancement causes portions of the U-shaped sections 316 of the staple 248 to flatten along the axis of the bridge 318 and front surface 320 of the actuator 306. Other portions of the U-shaped sections 316 extend from within the staple housing 214 such that the pointed ends 251 of the staple may penetrate the endograft 264 and the aortic wall 260.

Figure 20:
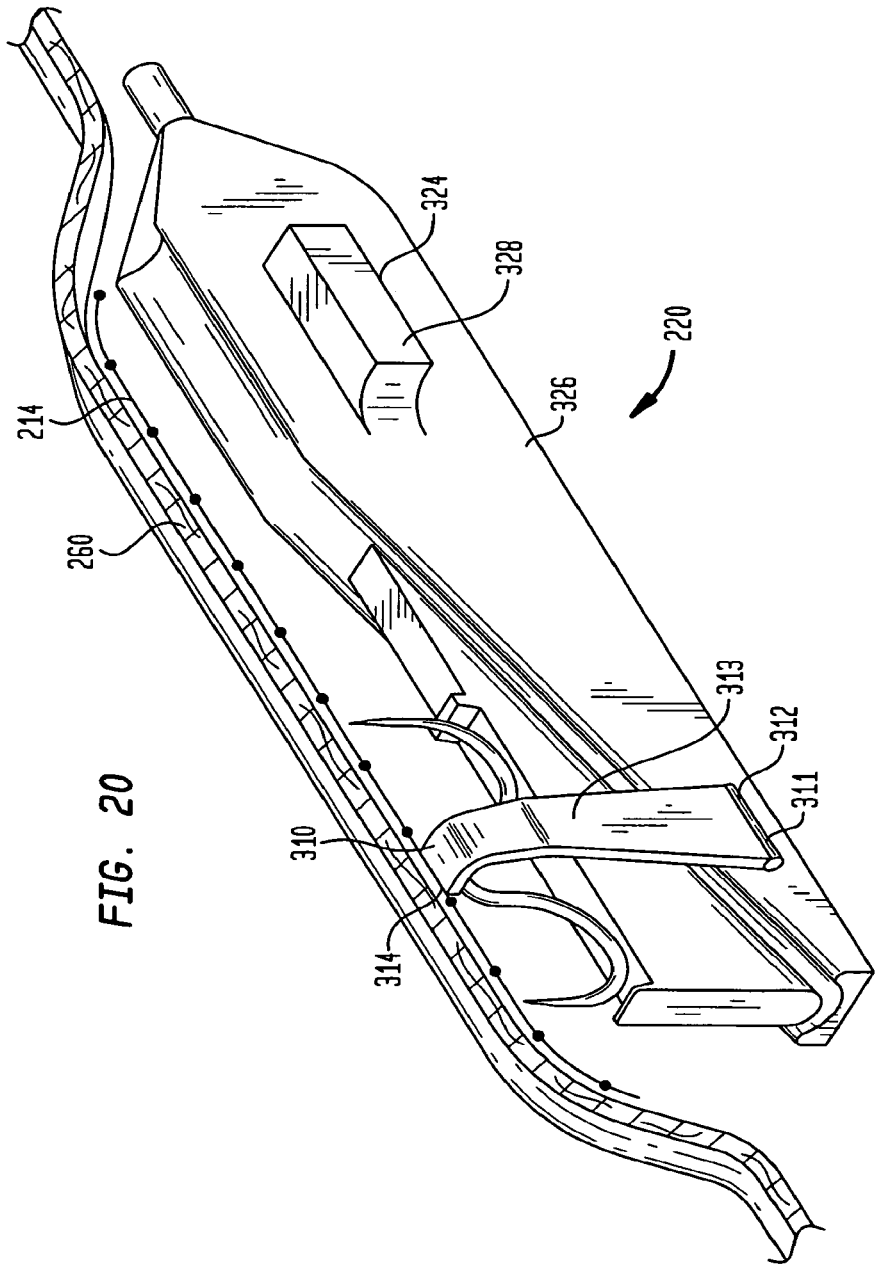
FIG. 20 depicts a perspective view of several internal components forming a portion of the stapler in accordance with the second embodiment of the present invention.

Referring briefly to FIG. 20, the pusher 220, in accordance with the second embodiment of the present invention, is shown with an elevated portion 324 on its side 326. The elevated portion 324 includes a transition area 328 ramping down toward the flat surface of the side 326 of the pusher 220. As the pusher 220 is displaced, the elevated portion 324 moves toward the middle portion 313 of the staple détente 310. Once the transition area 328 comes in contact with the middle portion 313 of the staple détente 310, the staple détente will be rotated about its first end 311 at hinge 312 to compress the spring 313 such that its second end 314 is no longer in contact with the staple 248.

Figure 19:
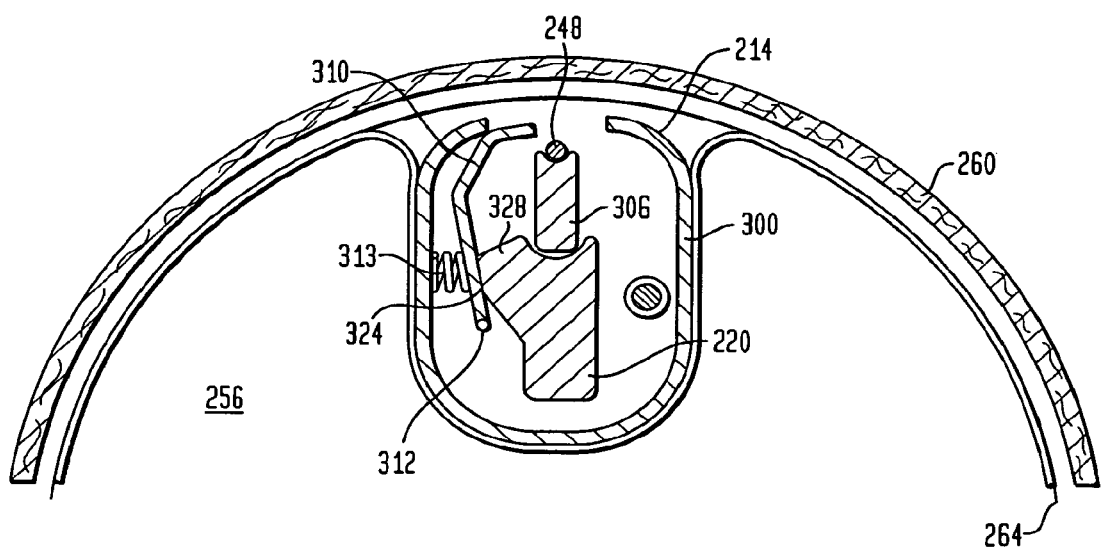
FIG. 19 depicts a cross-sectional view of the distal end of the staple housing of the stapler in accordance with the second embodiment of the present invention in the further advanced position of FIG. 18.

FIG. 19 depicts a cross-sectional view of a portion of the staple housing 214 of an endovascular stapler where the pusher 220 has been advanced such that the elevated portion 324 is in contact with the staple détente 310. It will be appreciated that advance of the pusher 220 and deflection of the staple détente 310 is conducted against the biasing force of the spring 313.

Figure 18:
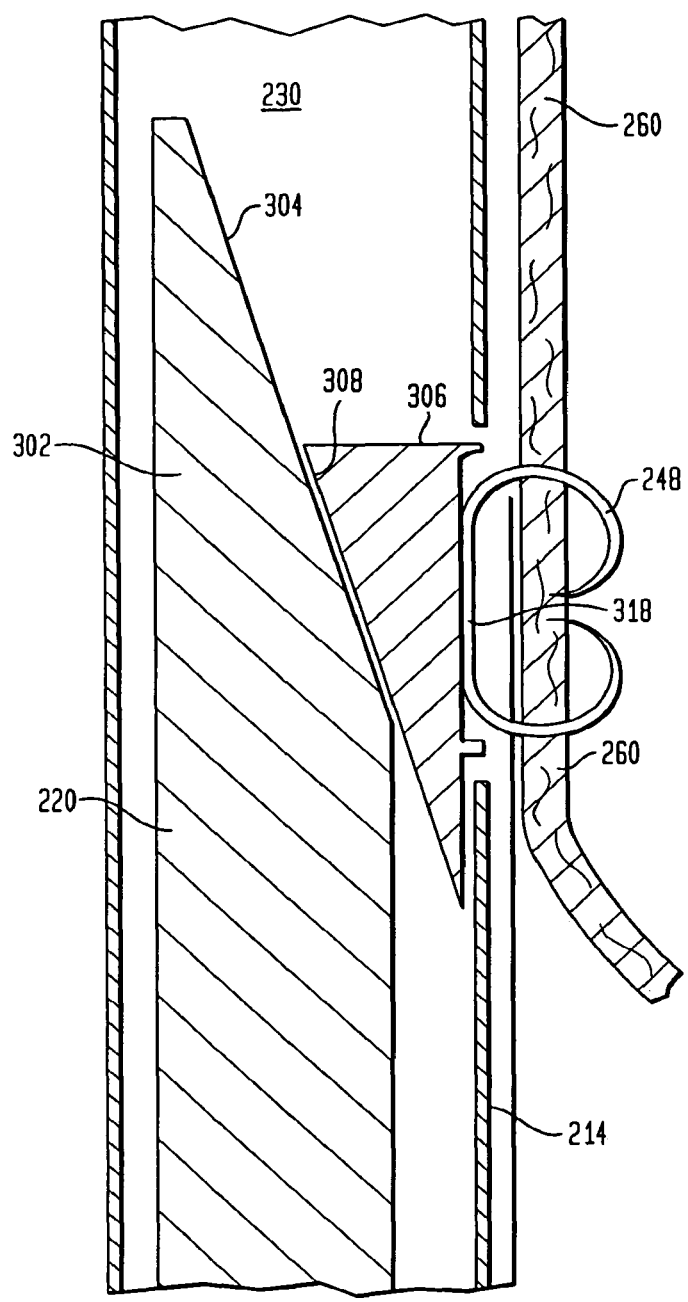
FIG. 18 depicts a longitudinal section view of the distal end of the staple housing of the stapler in accordance with the second embodiment of the present invention in an further advanced position.

FIG. 18 depicts a pusher 220 in its fully advanced position such that the staple détente 310 is no longer in contact with the staple 248. As shown in FIG. 18, it will be appreciated that prior to the staple détente 310 being rotated away from the staple 248, the U-shaped sections 316 of the staple 248 will have curved around such that the pointed ends 251 of the staple extend back into the aortic wall 260, and the bridge 318 is extended to include portions of the U-shaped sections, thus forming a closed staple.

The endovascular stapler disclosed with respect to the second embodiment of the present invention is intended to fire a single staple 248. As disclosed, if a subsequent staple 248 was required, the entire staple housing 214, possibly including the noncompliant balloon 256, would be removed from within the body so a second staple may be loaded. Once loaded, the staple housing 214 and, if necessary, the noncompliant balloon 256 may then be reinserted into the body such that a second staple 248 may be fired. This procedure may be repeated as necessary to arrest the migration of the endovascular graft or fully affix a new graft. Rather than reloading the endovascular stapler, a surgeon may choose to be provided with a plurality of endovascular staplers such that each may be utilized in succession without having to be reloaded. It will be appreciated that provision of numerous endovascular staplers saves time in the operating arena, where the duration of an operation is preferably minimized.

Figure 21:
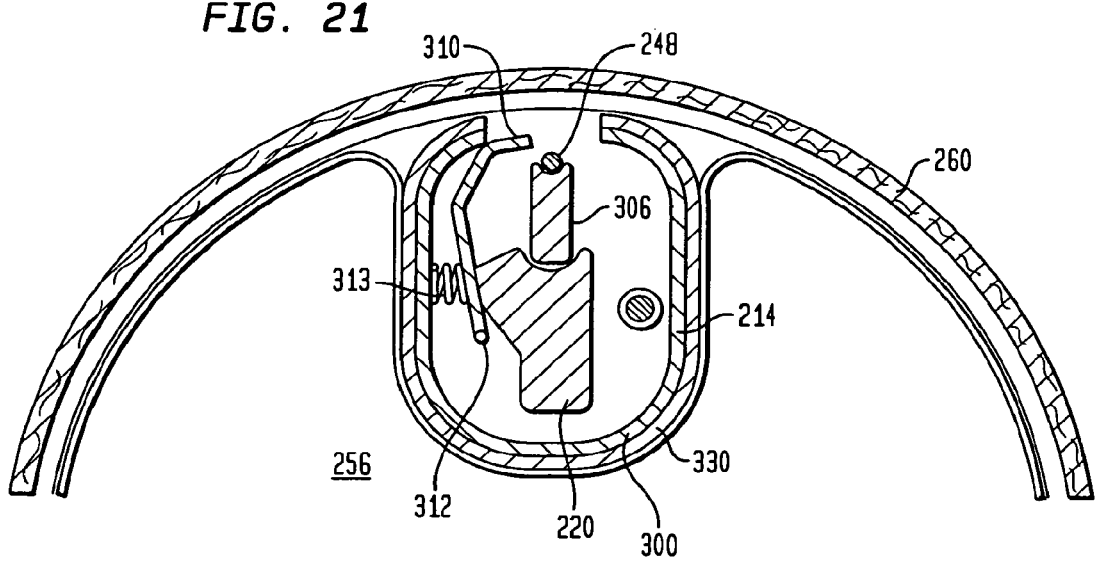
FIG. 21 depicts a cross-sectional view of the distal end of the stapler of the present invention in accordance with a third embodiment.

In a further embodiment, depicted in FIG. 21, a housing 330 may be disposed between the staple housing 214 and the noncompliant balloon 256. Such a housing 330 permits withdrawal of the staple housing 214, while leaving a cavity within the housing 330 wherein the staple housing may be returned after being reloaded with a subsequent staple (or where the housing of the second or subsequent stapler, may be inserted). The noncompliant balloon 256 may then be partially deflated to permit the staple exit area 258 to be rotated to a subsequent position for the firing of a subsequent staple 248. In this regard, additional staples 248 beyond the initial staple may be inserted in a relatively quick manner, as compared to other embodiments where the noncompliant balloon 258 may be removed and reinserted.

In further embodiments, additional staples may be mounted on a cartridge within the staple housing 214 to permit the automatic reloading of the device with additional staples. If so provided, a mechanism is included within the housing of the stapler to override the ratcheting function of the stapler trigger, such that the pusher may be retracted to the position shown in FIG. 15 from the position shown in FIG. 18. Once retracted into the position shown in FIG. 15, it is anticipated that a spring loaded stapler feed mechanism may reload the actuator with an additional staple automatically. Preferably, the automatic loading device would be capable of feeding up to seven staples, such that a total of eight staples may be fired without removal of the staple housing. It will be appreciated that eight staples are generally sufficient to connect the graft to a vessel. Of course, a loading device capable of supplying a greater number of staples may also be provided.

In further embodiments, multiple staples may be fired simultaneously from a single staple housing 214. In such embodiments, the staple housing 214 may include multiple staples 316 arranged radially about a centerline of the staple housing. The staples 316 may also be side-by-side in a linear relationship. Each of the staples 316 may be deployed simultaneously through interaction of the pusher 220 and the actuator 306. In such embodiments, the staple housing 214 preferably includes a staple détente 310 for each staple to be deployed. For example, in one embodiment employing two staples 316, a staple détente 310 may be mounted on each side of the pusher 220 by separate hinges 312. Each of the détentes 310 may be on opposite sides of the pusher 220, such that they can freely rotate without interfering with each other.

Figure 22A:
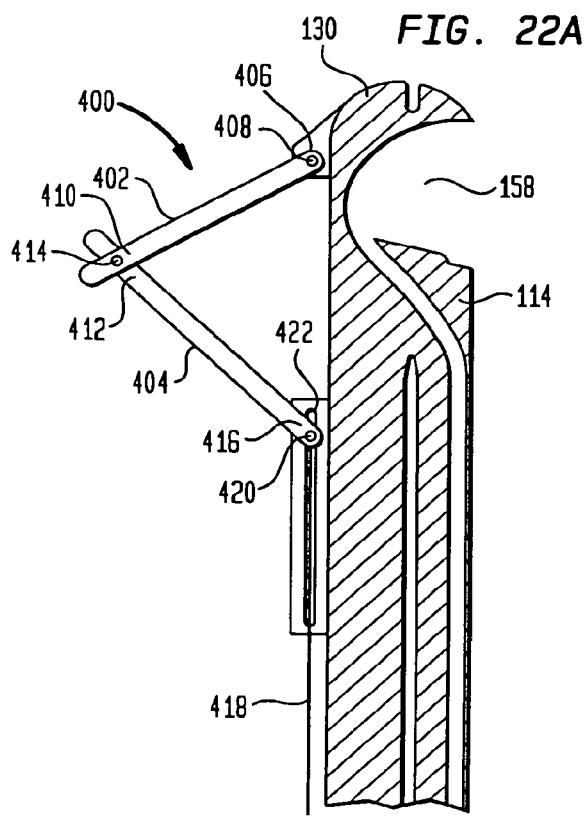
FIGS. 22a and 22b depict a triangular apparatus forming a portion of the staple housing which may be utilized in accordance with certain embodiments of the present invention, FIG. 22b depicting the triangular apparatus in a parallel relation and FIG. 22a depicting the triangular apparatus in an angled relation.
Figure 22B:
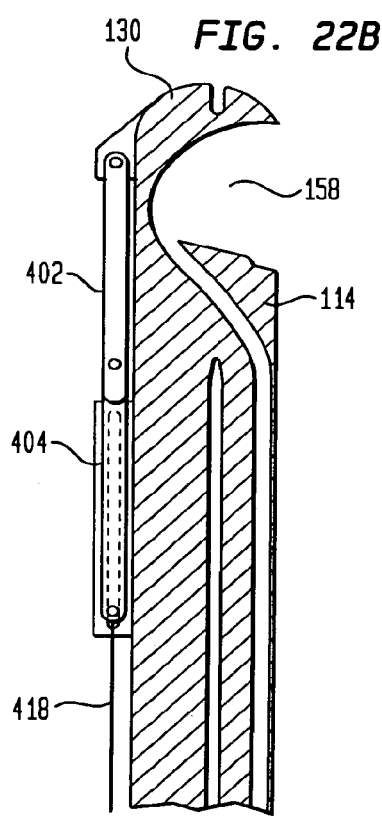

In addition to utilizing a balloon, such as the noncompliant balloon, to abut the staple exit area of the staple housing against the vessel wall or graft, other means may be employed. For example, as shown in FIGS. 22a and 22b, a simple triangular shaped apparatus 400 may be utilized. The apparatus 400 may comprise two elongate rods 402, 404. The first end 406 of the first rod 402 may be pivotally attached to the distal end 130 of the staple housing 114 by a pin 408. The second end 410 of the first rod 402 may be pivotally attached to the first end 412 of the second rod 404 by a pin 414. Finally, the second end 416 of the second rod 404 may be slidingly engaged to the staple housing 114 This sliding engagement may be achieved by utilizing a pin 420 slideable within a groove 422 created in the staple housing. A handle 418 may extend the length of the staple housing 114 to the housing 102 of the stapler 100.

Typically, if the rods 402, 404 are parallel to the longitudinal axis of the staple housing, such as shown in FIG. 22b, they will be adjacent to the staple housing 114, tight against its exterior wall. If the handle 418 is pushed forward toward the distal end 130 of the stapler 100, it will be appreciated that the pivot point between the first rod 402 and the second rod 404, located at pin 414, will be forced to extend from the exterior wall of the staple housing 114, as shown in FIG. 22a. If that pivot point 414 contacts the inner wall of a vessel, it will force the opposite side of the staple housing to move away from the portion of the inner wall contacting the pivot portion. Thus, the apparatus may be mounted opposite the staple exit 158 area to appose the staple exit area against the vessel wall in a predetermined area. Of course, multiple such triangular apparatuses, or parallelograms of greater than three sides comprising additional components, may also be utilized. In certain applications this type of displacement device may be preferred as it will not completely block or occlude the vessel, such that blood flow may continue.

In addition, although not shown, it will be appreciated that in other embodiments, the handle 418 may be positioned within a channel extending through the interior of the staple housing, similar to the balloon inflation channel previously discussed.

Figure 23A:
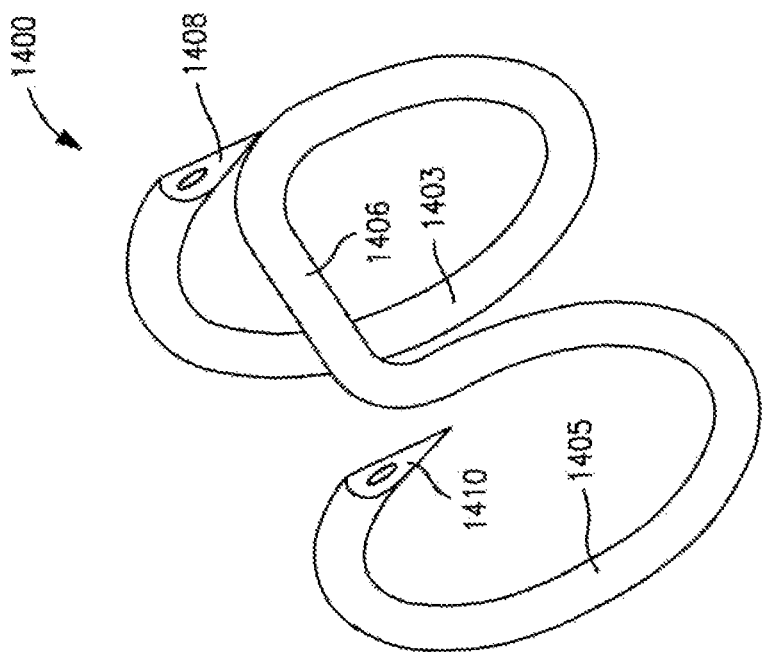
FIG. 23a depicts a perspective view of a staple capable of being utilized with a stapler in accordance with a further embodiment of the present invention.

The staples utilized throughout this invention may also be constructed of memory alloys, such as Nitinol. For example, staple 148a shown in FIG. 4 may be formed so as to create a loop, as shown in FIG. 12, in its natural condition. If so formed, the staple 148a should therefore be straightened prior to insertion into the endovascular stapler. Upon exiting the stapler, the staple 148a may then return to its natural condition owing particularly to the function of the memory metal, and not through bending or other shaping induced by the endovascular stapler. In the case of a memory metal, the internal staple guide serves to control the return of the staple to its default or natural condition such that the desired layers of endograft and vessel, as the case may be, are penetrated and repenetrated to achieve the desired fixation. FIG. 23a depicts a staple 1400 which may be utilized in conjunction with an endovascular stapler in accordance with a further embodiment of the present invention. The condition shown in FIG. 23a is the staple's 1400 natural condition. Preferably, the staple 1400 is constructed of a memory alloy such as Nitinol, as is commonly used in the art. Within the staple housing of an endovascular stapler, the staple 1400 will typically be deformed into the condition shown in FIG. 23b.

Figure 23B:
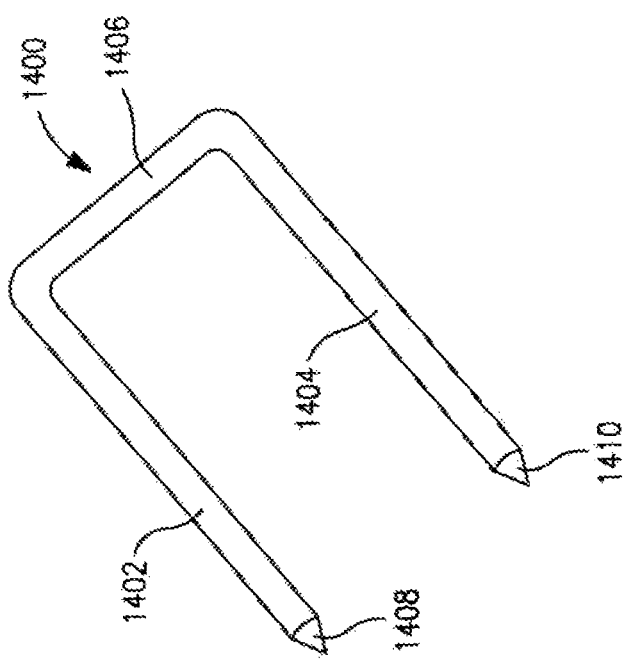
FIG. 23b depicts a perspective view of the staple shown in FIG. 23a following firing by the endovascular stapler.

As shown in FIG. 23b, the staple 1400 may be predominantly U-shaped in its deformed condition and may comprise a pair of legs 1402, 1404 connected by a central portion 406. Each of the pair of legs 1402, 1404 may terminate with spiked ends 1408, 1410.

Upon application into the endograft and vessel utilizing the techniques to be discussed, the staple 1400 may be permitted to return back to its natural condition into the shape shown in FIG. 23a. As shown, the legs 1402, 1404 may be bent into loops 1403, 1405 such that the spiked ends 1408, 1410 are adjacent to the central portion 1406. During the application process, the spiked ends 1408, 1410 may pierce the endograft and vessel so as to securely attach the two together.

Figure 24:
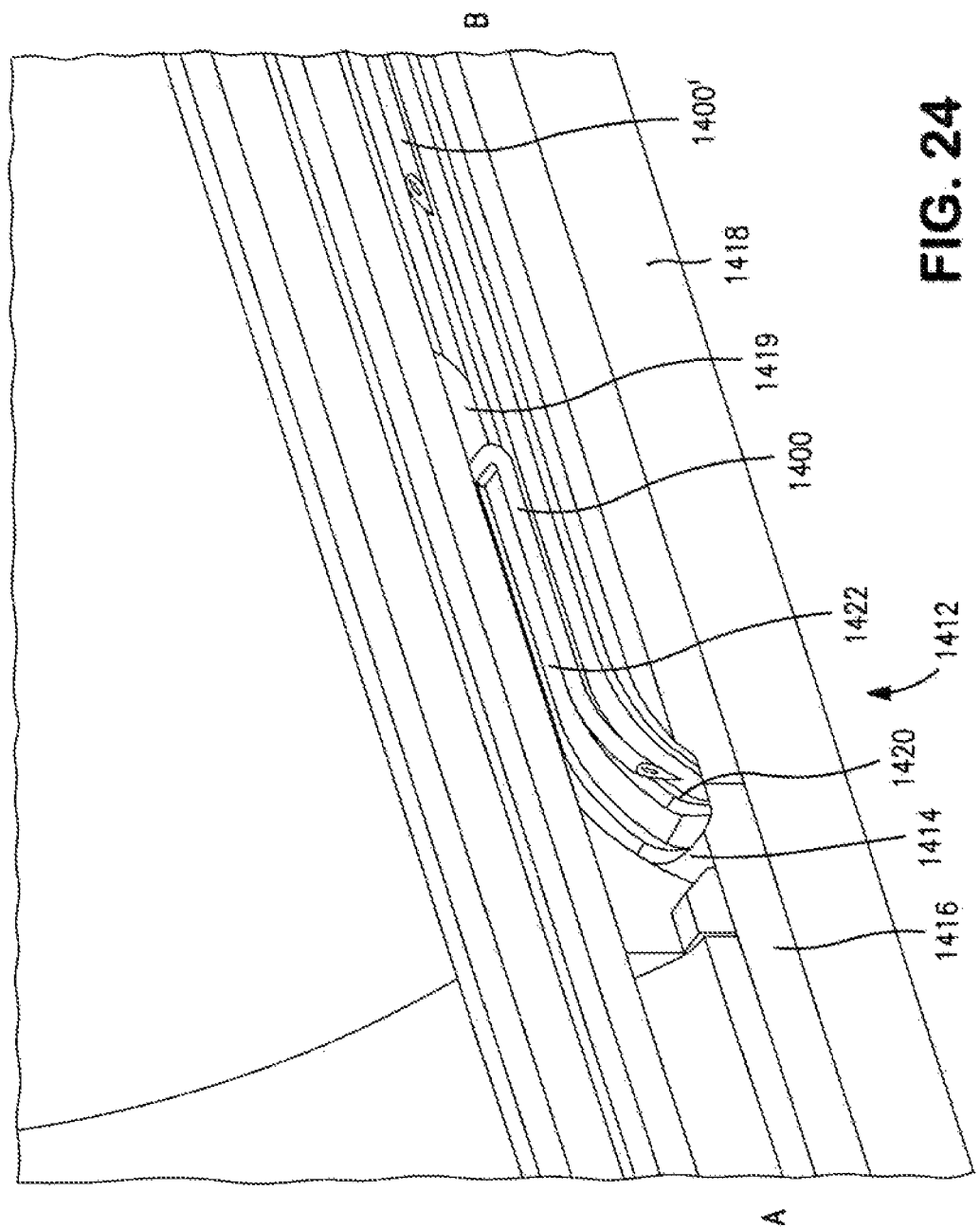
FIG. 24 depicts a cut-away view of a stapler housing firing the staple of FIG. 23a during an initial step of one embodiment of the present invention.

FIG. 24 depicts a cut-away view of the distal end of one embodiment of a stapler housing 1412 which may be utilized to deploy the staple 1400 shown in FIG. 23a. It will be appreciated that the orientation of the stapler housing 412 positioned in FIG. 24 is such that the patient's heart is located toward the side labeled B while an artery is located toward the side labeled A. The staple housing 1412 is preferably inserted into the body from the side labeled A, toward the heart.

As shown in FIG. 24, the staple housing 1412 may be placed such that its staple exit area 1414 is adjacent to an endograft 1416 intended to be connected to an aortic wall 1418. As discussed with respect to other embodiments of the present invention, a non-compliant balloon or other structure may be utilized to maintain this position.

Staples 1400, 1400' may be pre-placed in tandem within the staple housing 1412, prior to entry into the patient. It will be appreciated that the staples 1400, 1400' should be stretched from their natural condition prior to loading within the staple housing 1412 for certain embodiments of the present invention. Ratcheting the trigger of the stapler may pull the staple pusher 1419 toward the stapler body, rather than away from the stapler body as discussed with respect to previous embodiments.

As the staple 1400 is pushed toward the stapler body by the staple pusher 1419 in conjunction with the ratcheting trigger, the staple 1400 may travel along the arcuate path of the internal staple guide 1422 bounded partially by flanges 1420 and the limits of the internal staple guide.

Figure 25:
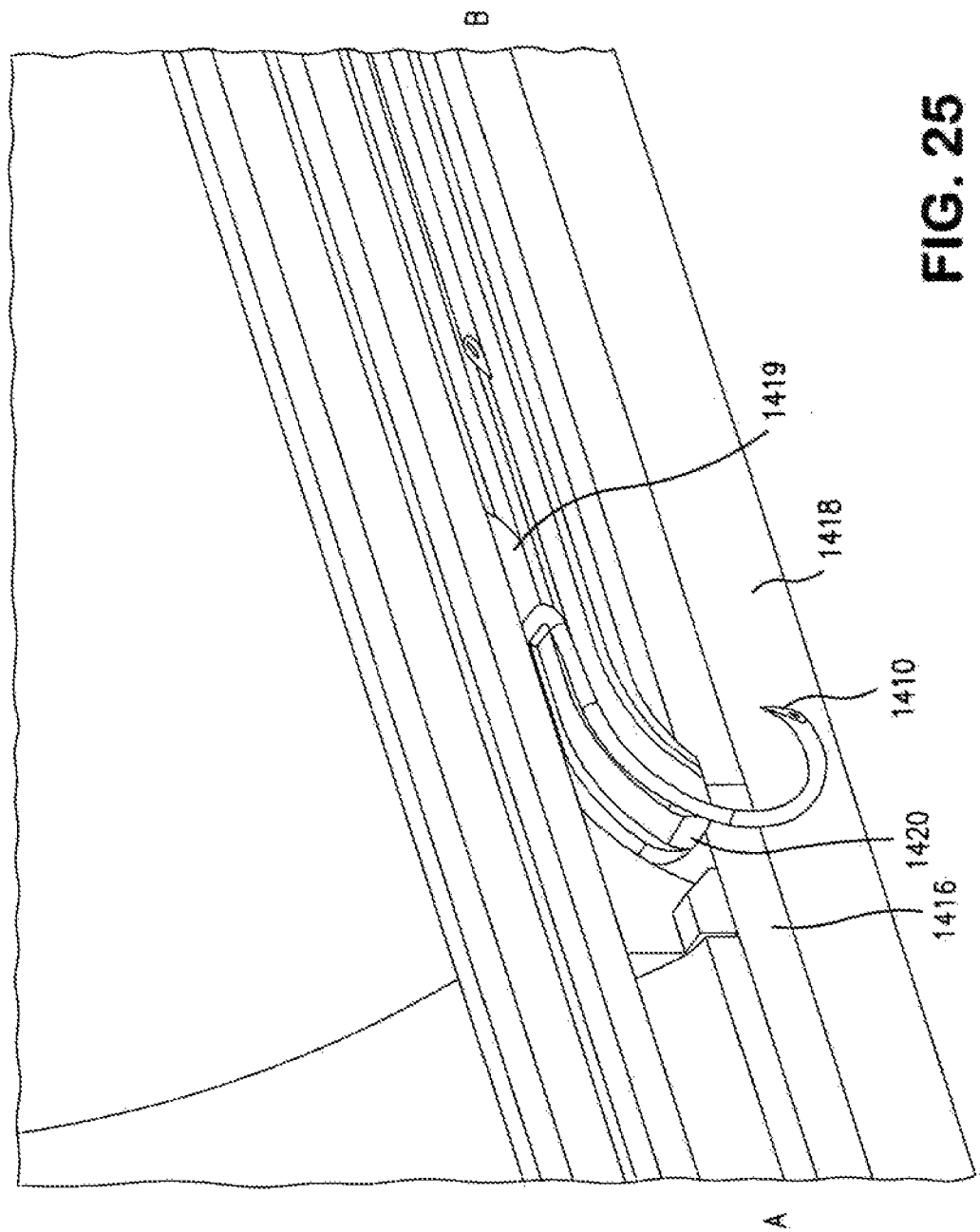

FIG. 25 depicts a further step in this process. As shown in FIG. 25, the straight legs 1402, 1404 of the staple 1400 may be permitted to form back into loops 1403, 1405 as the staple is pushed forward toward the staple exit area 1414. The leading spiked ends 1408, 1410 may therefore penetrate the endograft 1416 and the aortic wall 1418 as the loops 1403, 1405 are formed. Formation of such loops 1403, 1405 preferably secures the endograft 1416 to the aortic wall 1418. As with previous embodiments, it will be appreciated that a non-compliant balloon or other device may be utilized to ensure that the staple exit area 1414 is directly adjacent to the endograft 1416 to be stapled, and that the endograft is pressed against the aortic wall 1418.

Sizing of the loops 1403; 1405 may be advantageously controlled by selection of an appropriate staple 1400. Accordingly, a staple 1400 with a given loop diameter in its natural condition should return to that loop diameter upon discharge from the staple exit area 1414, regardless of the geometry of the internal staple guide 1422. In this regard, several sized staples may be utilized with a single endovascular stapler. Typically, staple loops 1403, 1405 range in size from approximately 2 mm to 6 mm, with 3 mm or 4 mm being a common size for fixation with the aorta. For smaller or thinner vessels, mm preformed loops are typical. Under normal conditions, the diameter or caliber of the various staples 1400 remains constant though their loops 1403, 1405 may vary in diameter. If required, the diameter or caliber of the staple 1400 may also be varied.

Figure 26:
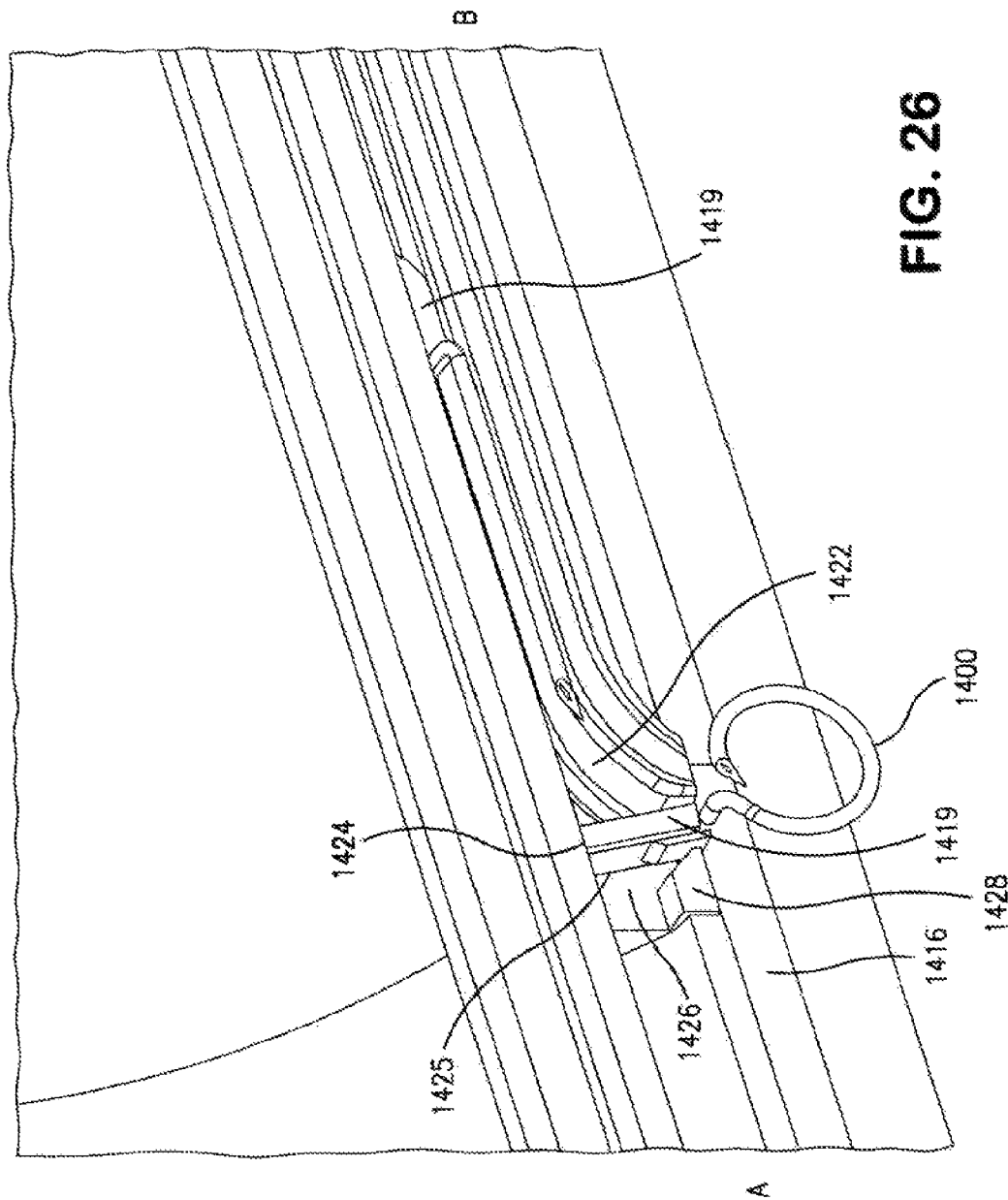

A further step in the method of deploying staple 1400 is shown in FIG. 26. As shown in FIG. 26, the staple pusher 1419 may be permitted to pivot about its heel 1424 into the open space 1425 provided in the internal staple guide 1422 near the staple exit area 1414 such that it preferably pushes the central portion 1406 of the staple 1400 completely against the endograft 1416 while the loops 1403, 1405 are formed. The natural action of the staple 1400 in forming the loops 1403, 1405 may also assist with securing the staple in place. The length of the pivoting portion 1426 of the staple pusher 1419 may be strategically designed to approximately equal the height of the internal staple guide 1422 such that upon rotation of approximately 90 degrees, the rotating portion 1426 of the staple pusher will fill the height of the internal staple guide to push the central portion 1406 of the staple completely against the endograft 1416.

Upon initiation of rotation of the rotating portion 1426 of the staple pusher 1419, the rotation portion may contact a fixed block 1428 provided for that purpose. The fixed block 1428 serves to further rotate the rotating portion 1426 of the staple pusher 1419 to angles beyond 90 degrees, such as is shown in FIG. 27 depicting a still further step in the method of deploying staple 1400.

As the rotating portion 1426 of the staple pusher 1419 is further rotated and positioned away from the staple exit area 1414, a second staple 1400' may be brought toward the staple exit area by a second staple pusher 1419' as shown in FIG. 27. The non-compliant balloon or similar device may then be manipulated to permit rotation of the staple housing 1412 such that the staple exit area 1414 is rotated or otherwise moved to a position adjacent to the previously deployed staple 1400. The non-compliant balloon or similar device may then be manipulated to push the staple exit area 1414 against the endograft 1416 and the endograft against the aortic wall 1418 in preparation of the firing of the second staple 1400'.

A partially cut-away view of staple 1400 completely installed into an endograft 1416 and a aortic wall 1418 is shown in FIG. 28. It will be appreciated that a series of staples 1400 installed side by side may be utilized to completely attach the endograft 1416 to the aortic wall 1418, around the circumference of the endograft. Typically, a series of six to eight staples 1400 may be utilized. As such, a single staple housing may house six to eight staples so the device need only be inserted into the patient once, while still being capable of driving the requisite number of staples 1400.

Referring back to FIG. 24, it will be appreciated that the staple 1400 is depicted as being driven away from the patient's heart, the heart being toward the direction labeled B in the figure. In other embodiments, the identical staple 1400 may be driven toward the heart. In such case, the ratcheting trigger will serve to push the staple pusher 1419, rather than pull the staple pusher. Installation of the endovascular driver is typically conducted in a direction toward the heart, regardless of the direction in which the staple 1400 is driven.

FIG. 29a depicts a staple 1450 which may be utilized in conjunction with an endovascular stapler in accordance with a still further embodiment of the present invention. The condition shown in FIG. 29a is the staple's 1450 natural condition. Preferably, the staple 1450 is constructed of a memory alloy such as Nitinol, as is commonly used in the art. Within the staple housing of an endovascular stapler, the staple 1450 will typically be deformed into the condition shown in FIG. 29b.

As shown in FIG. 29b, the staple 1450 may be deformed to be predominantly U-shaped with a tongue area 1452 between two legs 1454, 1456. Each of the pair of legs 1454, 1456 preferably terminates with spiked ends 1458, 1460.

The tongue area 1452 of staple 1450 generally comprises an inner U-shaped tongue 1462 formed between two outer U-shaped curves 1464, 1466 partially forming the legs 1454, 1456, as depicted in FIG. 29b.

As shown in FIG. 29a, in the staple's 1450 natural condition, the staple legs 1454, 1456 form loops 1468, 1470, the loops being bound between the spiked ends 1458, 1460 and the outer U-shaped curves 1464, 1466. As will be discussed, the tongue 1462 may be biased by the outer U-shaped curves 1464, 1466 to apply pressure to tissue and other material held between the tongue and the loops 1468, 1470.

Figure 30:
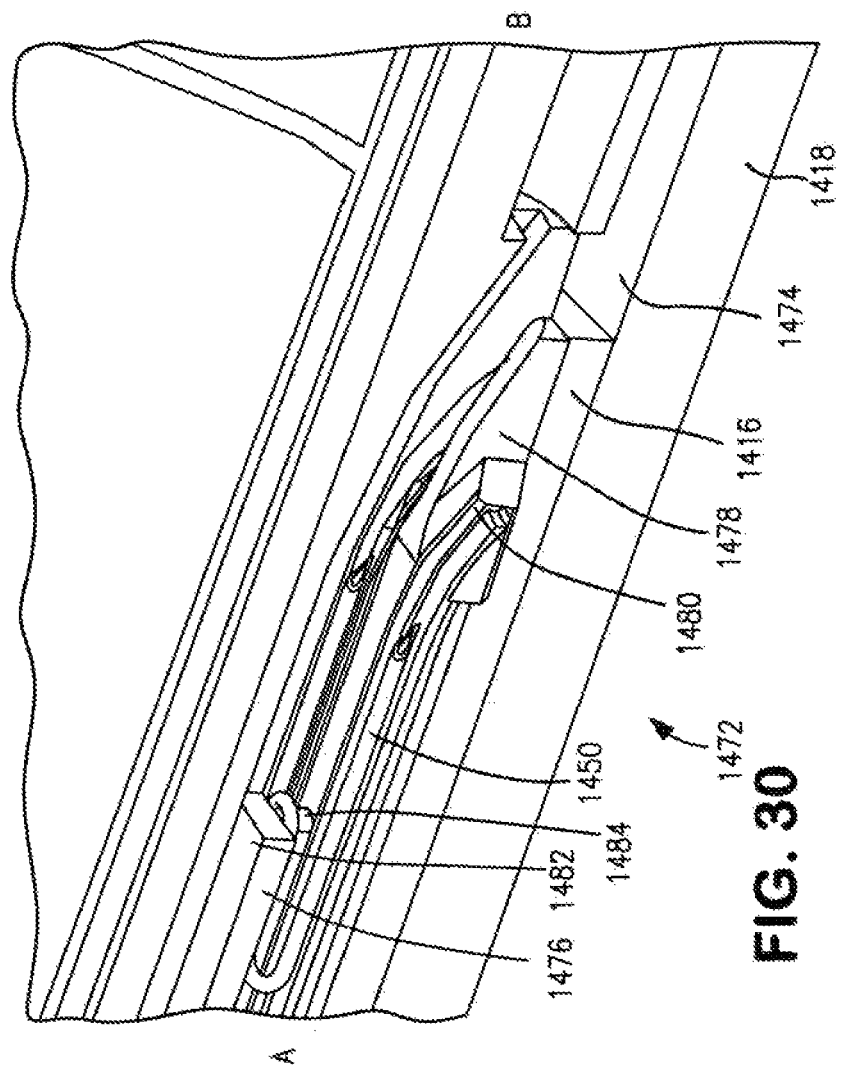
FIG. 30 depicts a cut-away view of a stapler housing firing the staple of FIG. 29a during an initial step of one embodiment of the present invention.

FIG. 30 depicts a cut-away view of the distal end of another embodiment of a stapler housing 1472 which may be utilized to deploy the staple 1450 shown in FIG. 29b. It will be appreciated that the orientation of the stapler housing 1472 positioned in FIG. 30 is such that the patient's heart is located toward the side labeled B while an artery is located toward the side labeled A. The staple housing 1472 is preferably inserted into the body from the side labeled A, toward the direction of the heart. In addition, it will be appreciated that the staples 1450 are fired in a direction toward the heart, although they may also be fired in the opposite direction in other embodiments.

As shown in FIG. 30, the staple housing 1472 may be placed such that the staple exit area 1474 is adjacent to an endograft 1416 intended to be connected to an aortic wall 1418. As discussed with respect to other embodiments of the present invention, a non-compliant balloon or other structure may be utilized to maintain this position.

Staples 1450 may be pre-placed in tandem within the staple housing 1472, prior to entry into the patient. Ratcheting the trigger of the stapler may therefore act to push the staple pusher 1476 away from the stapler body to fire the staple 1450 through the staple exit area 1474. As the staple 1450 is pushed away from the stapler body by the staple pusher 1476 in conjunction with the ratcheting trigger, the staple 1450 may travel along the arcuate path of the internal staple guide 1478 bounded partially by flanges 1480 and the limits of the internal staple guide.

The staple pusher 1476 in this embodiment preferably comprises an upper plate 1482 and a lower extension member 1484 extending downward therefrom. As shown in FIG. 30, the lower extension member is preferably sized and configured to fit within the tongue 1462 of the staple 1450, between the U-shaped curves 1464, 1466.

Figure 31:
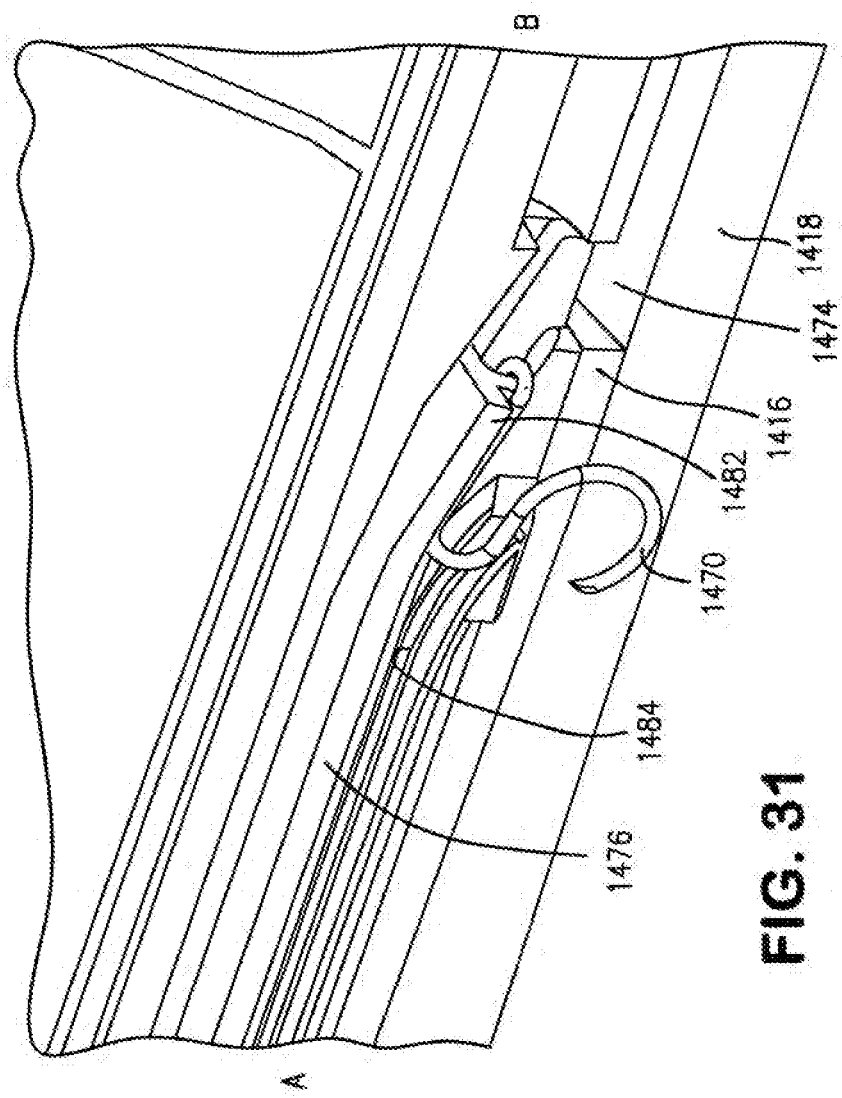

FIG. 31 depicts a further step in the process of firing staple 1450 in accordance with one embodiment of the present invention. As shown in FIG. 31, the straight legs 1454, 1456 of the staple 1450 may be permitted by the geometry of the internal staple guide 1478 to form back into loops 1468, 1470 as the staple is pushed away from the stapler body and into the staple exit area 1474. The leading spiked ends 1458, 1460 may penetrate the endograft 1416 and the aortic wall 1418 as the loops 1468, 1470 are formed. Formation of such loops 1468, 1470 preferably secures the endograft 1416 to the aortic wall 1418. As with previous embodiments, it will be appreciated that a non-compliant balloon or other device may be utilized to ensure that the staple exit area 1474 is directly adjacent to the endograft 1416 to be stapled, and that the endograft is pressed against the aortic wall 1418.

Figure 32:
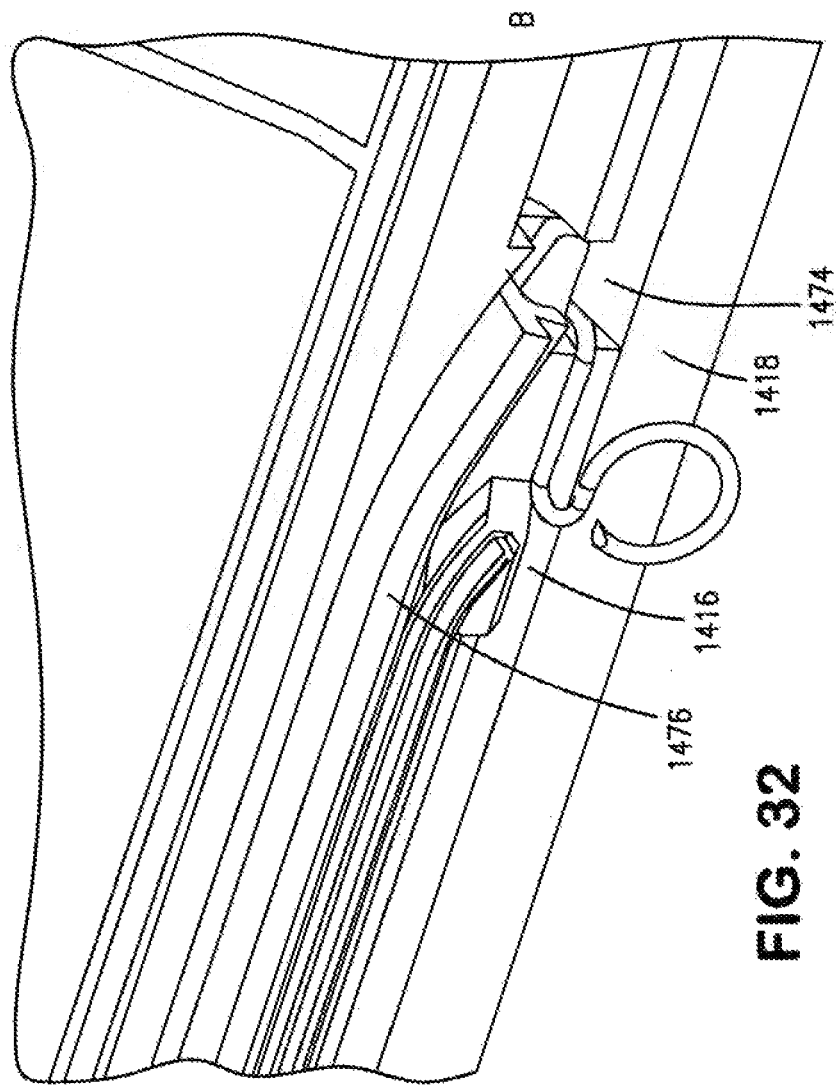
Figure 33:
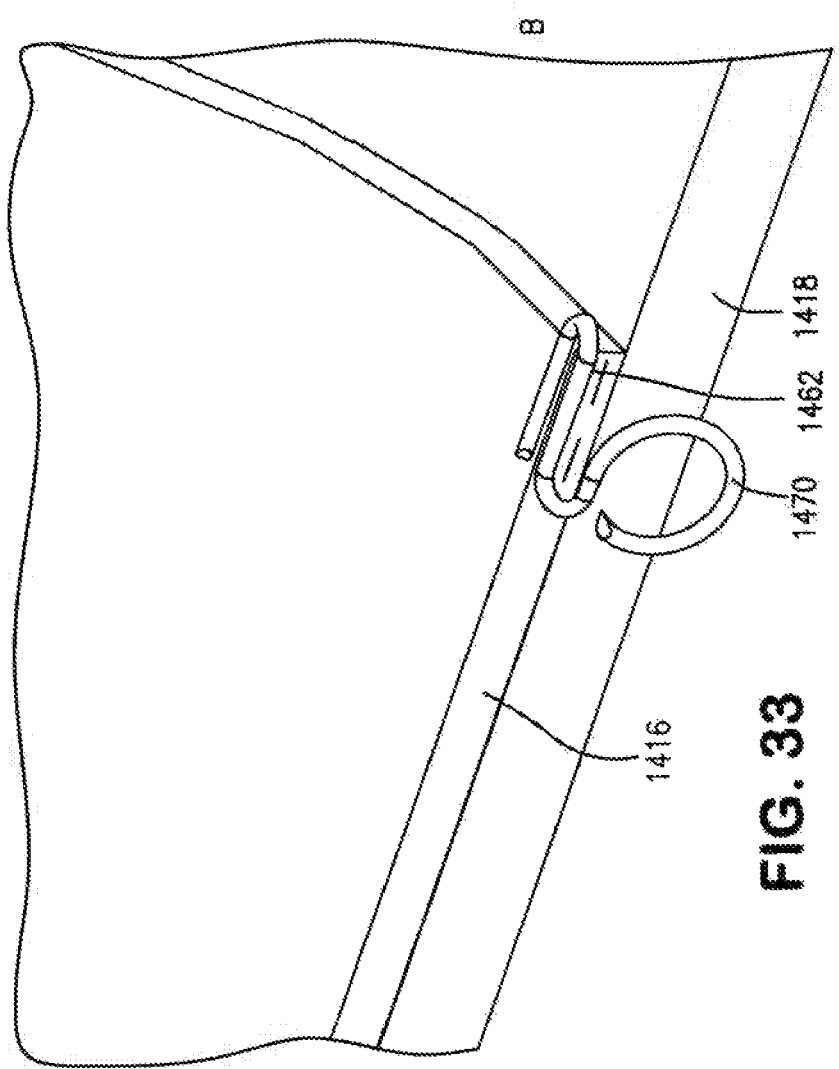
FIG. 33 depicts a cut-away view of a the staple of FIG. 29a fired into and endograft and an aortic wall.

A further step in the method of deploying staple 1450 is shown in FIG. 32. As shown in FIG. 32, the staple pusher 1476 extends into the staple exit area 1474, releasing the tongue 1462 of the staple 1450. The staple 1450 is therefore left securing the endograft 1416 to the aortic wall 1418, as shown in FIG. 33.

As with other embodiments, the diameter of the loops 1468, 1470 may vary. Staples 1450 preselected with a chosen loop diameter may be loaded into the endovascular stapler prior to the surgical procedure. Staples 1450 having various sized loops may be utilized with a single endovascular stapler. The varying loop sizes may affect the excursion required by the pusher 1476 to deploy a staple 1450, but that is easily remedied by the surgeon in practice. In this regard, each staple length may be associated with a predetermined number of trigger strokes for deployment so the surgeon becomes aware of when the staple is released. Otherwise, visual indication may be provided such as by ultrasound, x-ray, or other known methods.

One feature of staple 1450, and those like it having cantilevered tongues, is that the placement of the staple in relation to the edge 1417 of the endograft 1416 need not be precise. It will be appreciated that deviations from ideal placements may be accommodated by the tongue 1462. For example, the tongue 1462 includes a length L. Typically, length L is on the order of approximately 1-10 mm, preferably 5 mm. So long as the edge 1417 of the endograft 1416 is beneath the tongue 1462, the placement of the staple 1450 should be considered successful. In this regard, the edge 1417 of the endograft 1416 may be secured beneath the tongue 1462, and will not freely open. The tongue 1462 will therefore secure any "flapping," or otherwise unsecured portions of the endograft.

Figure 34:
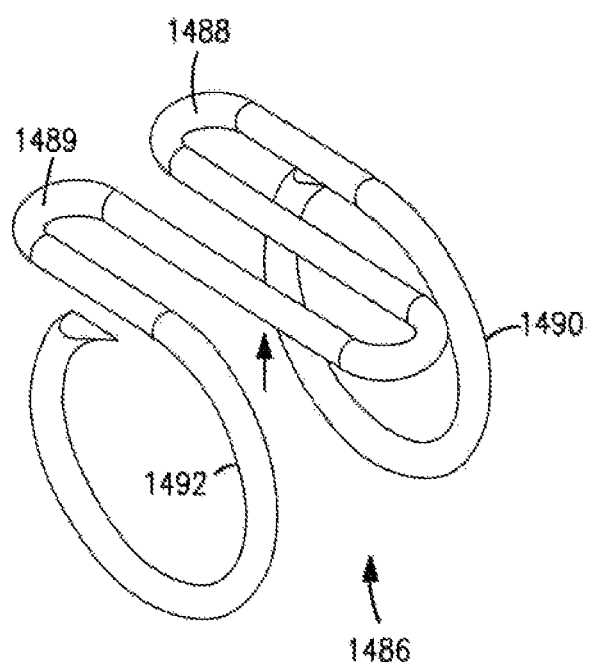
FIG. 34 depicts a perspective view of a deformed staple following firing by the endovascular stapler in accordance with another embodiment of the present invention.

FIG. 34 depicts a perspective view of yet another embodiment of a staple 1486 in its natural condition. Staple 1486 exhibits many of the advantageous of staple 1450 depicted in FIG. 29a, by virtue of its having a pair of tongues 1488, 1489. Accordingly, staple 1486 is capable of applying greater pressure to material trapped between the tongues 1488, 1489 and the loops 1490, 1492 by virtue of the added material.

Figure 35:
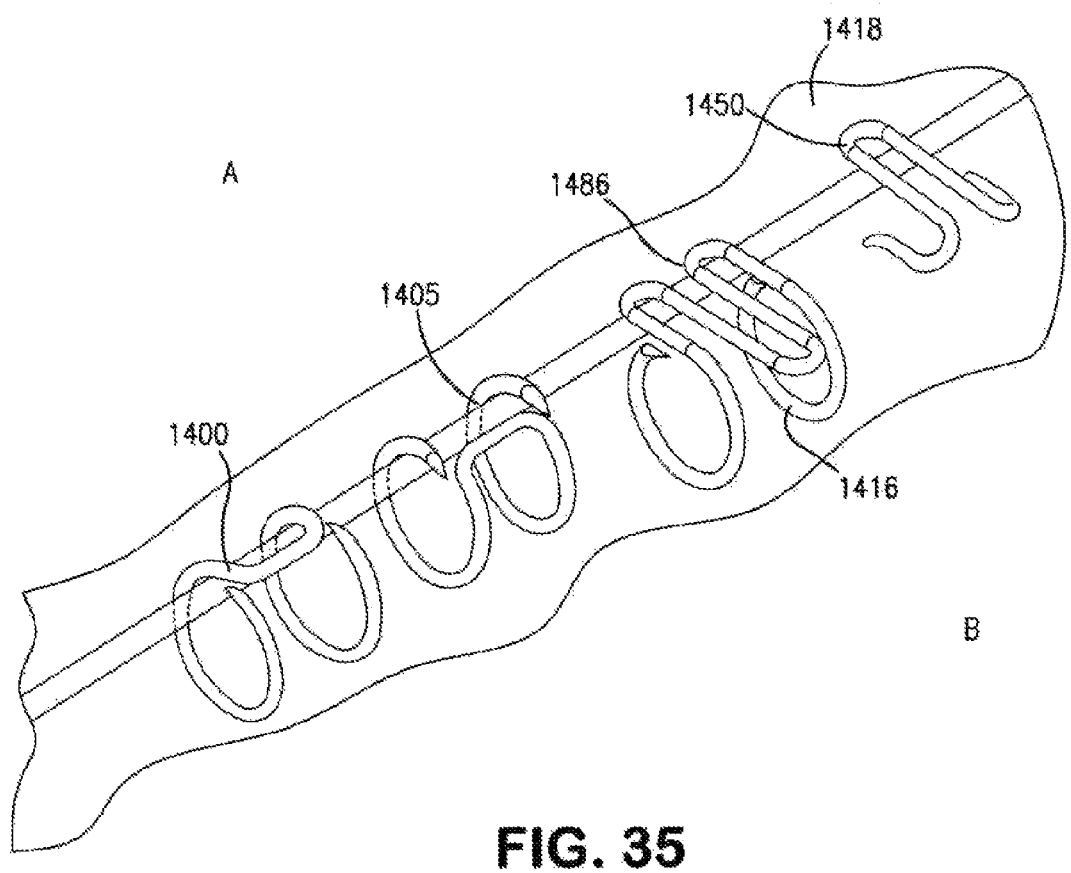
FIG. 35 depicts a perspective view of several deformed staples following firing by endovascular staplers in accordance with several embodiments of the present invention.

FIG. 35 depicts an array of various embodiments of staples connecting an endograft 1416 to an aortic wall 1418, including staples 1400 as shown in FIG. 23b, staple 1450 as shown in FIG. 29b, and staple 1486 as shown in FIG. 34. It will be appreciated that the staples shown have been fired from different directions, the two inner staples being fired from a direction corresponding to letter A, near the heart, and the two outer staples being driven from a direction corresponding to letter B, farthest from the heart. Nevertheless, each staple is capable of achieving the desired result in an effective manner.

It will be appreciated that the staples shown and otherwise described throughout this may have a varied number of spiked piercing points in their various embodiments. For example, the staple 148a shown in FIG. 4 includes a single pointed end 150 while the staple 1400 shown in FIG. 23a includes a pair of pointed ends 1408, 1410. Other embodiments of staples may include additional pointed ends, such as three or more. Each of these ends may be connected by a central portion 1406. Accordingly, and as an example, a single staple may include a first leg having a pointed end connected to a first central member, a second leg having a pointed end connected on one side to the first central member and on another side to a second central member, and a third leg having a pointed end connected to the second central member, such that the staple forms a W shape with three pointed ends, similar to that found on the head of a trident. It will also be appreciated that the staple legs need not be along the same plane, and may be curved or otherwise angled with respect to each other to conform more closely to the shape of the vessel in which they are intended to be applied. The most limiting factor in determining the number of piercing points, and the curvature of the staple, is practicality of the application.

As previously discussed, the various embodiments of the endovascular staplers described in accordance with the present invention typically include a non-compliant balloon or other biasing mechanism to ensure that the staple exit area of the endovascular staple is secure against the endograft or vessel wall. Another embodiment of a biasing device which may be utilized for this purpose is shown in FIGS. 36a through 38b.

Figure 36A:
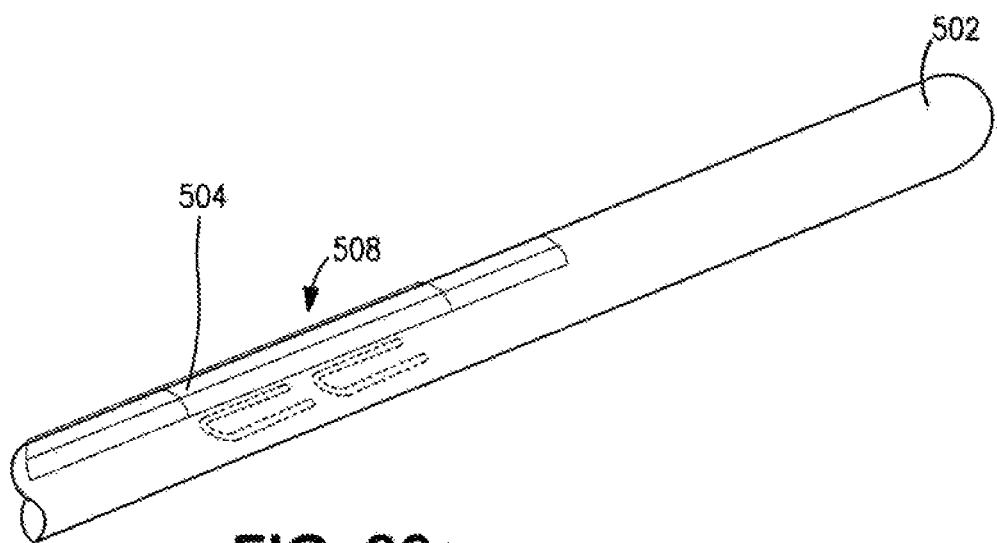
FIG. 36a depicts a perspective view of the distal end of an endovascular stapler in accordance with another embodiment of the present invention.
Figure 36B:
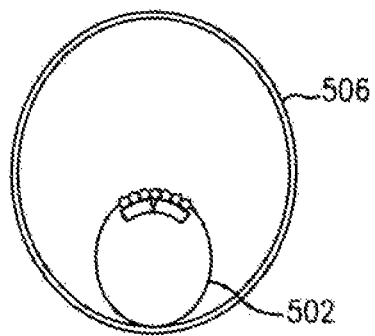
FIG. 36b depicts a cross-sectional view of the distal end of the endovascular stapler shown in FIG. 36a inserted within a vessel.

As shown in FIG. 36a, the distal end 500 of an endovascular stapler may include a recessed housing 504 containing a collapsed biasing mechanism 508 there within. Optimally, the biasing mechanism may be completely contained within the endovascular stapler assembly so as to not increase the overall profile of the endovascular stapler. FIG. 36b depicts a cross-sectional view of an aorta or other vessel with the distal end 502 of an endovascular stapler there within.

Figure 37A:
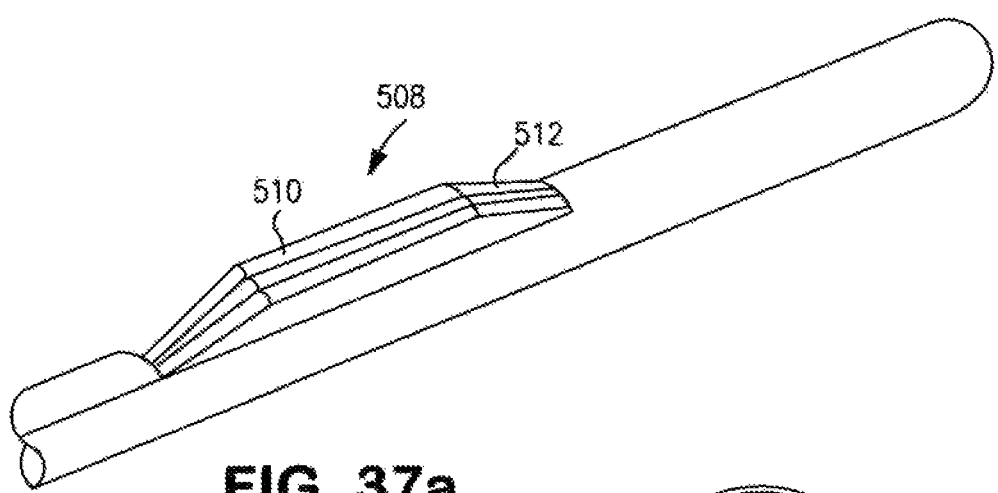
FIG. 37a depicts a perspective view of the distal end of the endovascular stapler shown in FIG. 36a, with its associated biasing mechanism partially deployed.
Figure 37B:
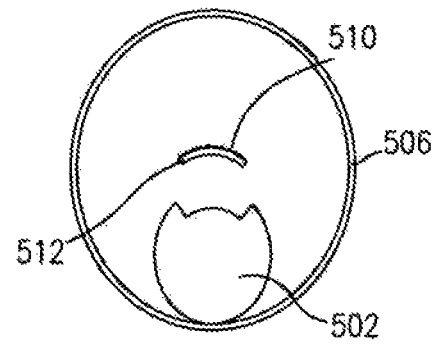
FIG. 37b depicts a cross-sectional view of the distal end of the endovascular stapler shown in FIG. 37a inserted within a vessel.

An initial stage of deployment of the biasing mechanism 508 is shown in FIG. 37a. In order to deploy the biasing mechanism 508, the endovascular stapler may include a suitable activation mechanism, such as a rotating knob, sliding pusher, spring loaded trigger, or other device. The biasing mechanism shown comprises a non-compliant balloon 510 tethered to the distal end 502 of an endovascular stapler by spokes 512. Upon deployment of the biasing mechanism 508, the non-compliant balloon 510 will begin to extend away from the distal end 502 of the endovascular stapler, as shown in the cross-sectional view of FIG. 37b. Typically, one or more of the spokes 512 will be hollow and will be in fluid communication with the non-compliant balloon 510, such that filling of the balloon may be achieved through the spoke. The spokes are also preferably rigid so as to offset the balloon from the distal end 502 of the endovascular stapler. Spokes 512 may be constructed of various biocompatible materials, including metals and plastics.

Figure 38A:
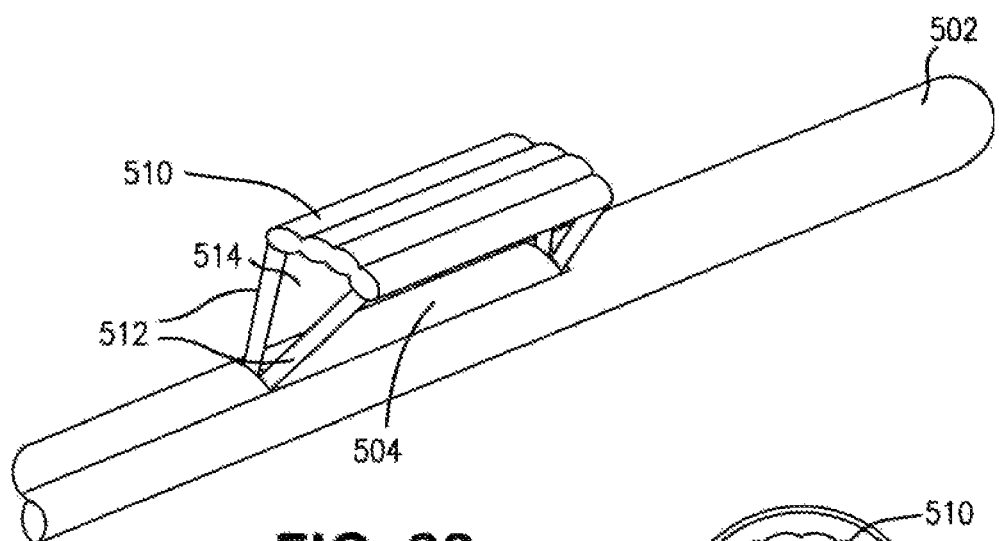
FIG. 38a depicts a perspective view of the distal end of the endovascular stapler shown in FIG. 36a, with its associated biasing mechanism fully deployed; and, FIG. 38b depicts a cross-sectional view of the distal end of the endovascular stapler shown in FIG. 38a inserted within a vessel.
Figure 38B:
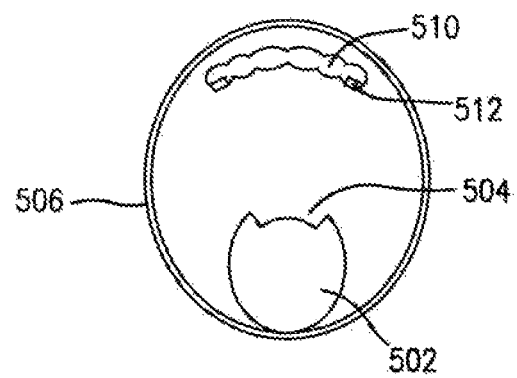

FIG. 38a depicts a fully deployed balloon 512. It will be appreciated that the spokes 512 create a web 514 therebetween when fully deployed such that blood or other fluid may flow therethrough. As shown in FIG. 38b, the balloon 510 and associated spokes 512 serve to ensure that the staple exit area of the endovascular stapler abuts the vessel and/or endograft. Preferably, the staple exit area is positioned directly opposite to the biasing mechanism 508, to maximize the pressure available.

It will be appreciated that the deployment mechanism (not shown) of the balloon 510 is preferably sensitive enough to expand the balloon fully, and then partially deflate the balloon so as to enable the endovascular stapler to rotate. Following rotation, the balloon 510 should then again be capable of inflation, such that a subsequent staple may be fired.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In this regard, elements such as the trigger have been described in a particular manner. It is to be understood that the trigger mechanism and others like it, may be manufactured differently. For example, in lieu of a trigger, a simple dial advancement mechanism may be utilized to displace the pusher within the stapler cavity. If so provided, the gear ratio of the dial may be designed such that a given number of turns of the dial will advance the staple pusher a distance coordinated with the length of a single staple.

The invention claimed is:

1. A method of attaching an endograft to a vessel wall with an endovascular stapler having a distal end and a proximal end with a biasing mechanism associated therewith, said method comprising:

inserting the distal end of the endovascular stapler into the endograft;

activating the biasing mechanism so as to push the distal end of the endovascular stapler against the endograft;

discharging through a trigger mechanism and/or staple housing a first staple having a pair of legs connected by a central portion from the endovascular stapler into the endograft and vessel such that the staple legs form a pair of equi-distantly spaced circular parallel loops connected by the central portion when in a natural condition, and having a pair of straight parallel legs joined by said central portion when in a deformed condition; said staple transformed from said deformed condition to said natural condition as it moves forward during discharge along a staple channel, and said parallel loops of said staple are formed in a direction that is substantially parallel to a longitudinal direction of said staple channel and not toward each other, the parallel loops being formed inwardly and perpendicular to the central portion of the staple, and further including respective pointed ends oriented in the same direction perpendicular to the central portion of the staple, forming a 3-dimensional staple structure.

2. The method of claim 1, further comprising the steps of:
partially deactivating the biasing mechanism to permit rotation of the distal end of the endovascular stapler;
rotating the distal end of the endovascular stapler;
reactivating the biasing mechanism so as to push the distal end of the endovascular stapler against the endograft;
discharging a second staple having a pair of legs connected by a central portion from the endovascular stapler into the endograft and vessel such that the staple legs of the second staple form a pair of circular loops connected by the central portion of the second staple.

3. The method of claim 1, wherein the first staple is constructed from a memory alloy.

4. The method of claim 3, wherein the legs of the first staple are predominantly straight while within the stapler prior to said step of discharging.

5. The method of claim 4, wherein the natural condition of the first staple is where the legs form circular loops.

6. The method of claim 5, wherein the step of discharging permits the first staple to return to its natural condition.

7. The method of claim 5, wherein said step of discharging serves to advance a staple pusher within said stapler for discharging the first staple.

8. The method of claim 7, wherein the first staple advances along a staple guide, the staple guide retarding the return of the first staple to its natural condition.

9. The method of claim 4, wherein the straight legs are substantially parallel to the longitudinal axis of the endograft during said step of inserting.

10. The method of claim 1, wherein the endovascular stapler includes a removable cartridge containing a plurality of staples, each of the staples having a pair of legs connected by a central portion.

11. The method of claim 10, wherein the legs of the plurality of staples are predominantly straight while within the stapler cartridge.

12. The method of claim 11, wherein a natural condition of the plurality of staples is where the legs form circular loops, and said step of discharging permits the first staple to return to its natural condition.

13. The method of claim 10, wherein the cartridge is replaceable.

14. The method of claim 1, wherein the vessel flows blood from a heart and said step of discharging drives the first staple toward the heart against the direction of blood flow.

15. The method of claim 14, wherein said step of discharging is conducted by a trigger mechanism that pushes a staple pusher.

16. The method of claim 1, wherein the vessel flows blood from a heart and said step of discharging drives the first staple away from the heart in the direction of blood flow.

17. The method of claim 16, wherein said step of discharging is conducted by a trigger mechanism that pulls a staple pusher.

18. The method of claim 1, wherein the step of discharging advances the first staple through a staple exit area, the staple exit area being radio opaque.

19. A method of attaching an endograft to a vessel wall with an endovascular stapler having a distal end and a proximal end with a biasing mechanism associated therewith, said method comprising:
inserting the distal end of the endovascular stapler into the endograft;
activating the biasing mechanism so as to push the distal end of the endovascular stapler against the endograft;
discharging through a trigger mechanism and/or staple housing a first staple having a pair of legs connected by a central portion from the endovascular stapler into the endograft and vessel such that the staple legs form a pair of circular parallel loops connected by the central portion when in a natural condition, and having a pair of straight parallel legs joined by said central portion when in a deformed condition; said staple transformed from said deformed condition to said natural condition as it moves forward during discharge along a staple channel, and said parallel loops of said staple are formed in a direction that is substantially parallel to a longitudinal direction of said staple channel and not toward each other, the parallel loops being formed inwardly and perpendicular to the central portion of the stable forming a 3-dimensional staple structure;
wherein the first staple is constructed from a memory alloy;
wherein the legs of the first staple are predominantly straight while within the stapler prior to said step of discharging;
wherein the natural condition of the first staple is where the legs form circular loops;
wherein said step of discharging serve to advance a staple pusher within said stapler for discharging the first staple;
wherein the first staple advances along a staple guide, the staple guide retarding the return of the first staple to its natural condition; and
wherein the staple pusher includes a pivoting portion and the step of discharging rotates the pivoting portion into the central portion of the first staple such that the central portion of the first staple abuts the endograft.

* * * * *